US 10,641,690 B2

(12) United States Patent
Brovold

(10) Patent No.: US 10,641,690 B2
(45) Date of Patent: May 5, 2020

(54) MATERIAL PERFORMANCE TESTING INCLUDING IMPROVED LOAD DETECTION

(71) Applicant: Troxler Electronic Laboratories, Inc., Research Triangle Park, NC (US)

(72) Inventor: Shawn Brovold, Edina, MN (US)

(73) Assignee: Troxler Electronic Laboratories, Inc., Research Triangle Park, NC (US)

(*) Notice: Subject to any disclaimer, the term of this patent is extended or adjusted under 35 U.S.C. 154(b) by 0 days.

(21) Appl. No.: 15/864,465

(22) Filed: Jan. 8, 2018

(65) Prior Publication Data

US 2018/0195941 A1 Jul. 12, 2018

Related U.S. Application Data

(60) Provisional application No. 62/443,628, filed on Jan. 6, 2017.

(51) Int. Cl.
| | |
|---|---|
| *G01N 3/08* | (2006.01) |
| *G01N 33/42* | (2006.01) |
| *G01N 3/20* | (2006.01) |

(52) U.S. Cl.
CPC ............... *G01N 3/08* (2013.01); *G01N 3/20* (2013.01); *G01N 33/42* (2013.01); *G01N 2203/0062* (2013.01)

(58) Field of Classification Search
CPC .. G01N 3/08; G01N 3/20; G01N 3/26; G01N 3/28; G01N 33/42; G01N 33/38; G01N 2203/0062
See application file for complete search history.

(56) References Cited

U.S. PATENT DOCUMENTS

| | | | | | |
|---|---|---|---|---|---|
| 5,048,320 | A | * | 9/1991 | Mitsuhashi | G01M 7/08 73/12.09 |
| 6,389,876 | B1 | * | 5/2002 | Tanimura | G01N 3/06 73/12.01 |
| 8,825,423 | B1 | * | 9/2014 | Brovold | G01N 3/08 702/41 |

OTHER PUBLICATIONS

Standard Method of Test for Determining the Fracture Potential of Asphalt Mixtures Using Semicircular Bend Geometry (SCB) at Intermediate Temperature, American Association of State Highway and Transportation Officials, Aug. 2016, 13 pages.

(Continued)

*Primary Examiner* — Lisa M Caputo
*Assistant Examiner* — Nigel H Plumb
(74) *Attorney, Agent, or Firm* — NK Patent Law

(57) ABSTRACT

A material testing apparatus includes an actuator to apply a force to a load head according to electronic control signals. The load head supplies a load to a material specimen in a first dimension. A plurality of load line displacement (LLD) reference points extend radially outward from the load head; and a plurality of LLD measuring devices correspond to the plurality of LLD reference points. Each LLD measuring device is positioned to detect a position of a corresponding LLD reference point along the first dimension and is configured to transmit position signals to a controller programmed to perform a performance test on the material specimen using feedback control based on a combination of the position signals, including an average of the position signals.

16 Claims, 23 Drawing Sheets

(56) References Cited

OTHER PUBLICATIONS

Determining the Fracture Potential of Asphalt Mixtures Using the Illinois Flexibility Index Test (I-FIT), Illinois Test Procedure 405, Jan. 2016, 12 pages.
Standard Test Method for Determining Fracture Energy of Asphalt-Aggregate Mixtures Using the Disk-Shaped Compact Tension Geometry, ASTM International, Designation: D 7313-07, 2007, 7 pages.

* cited by examiner

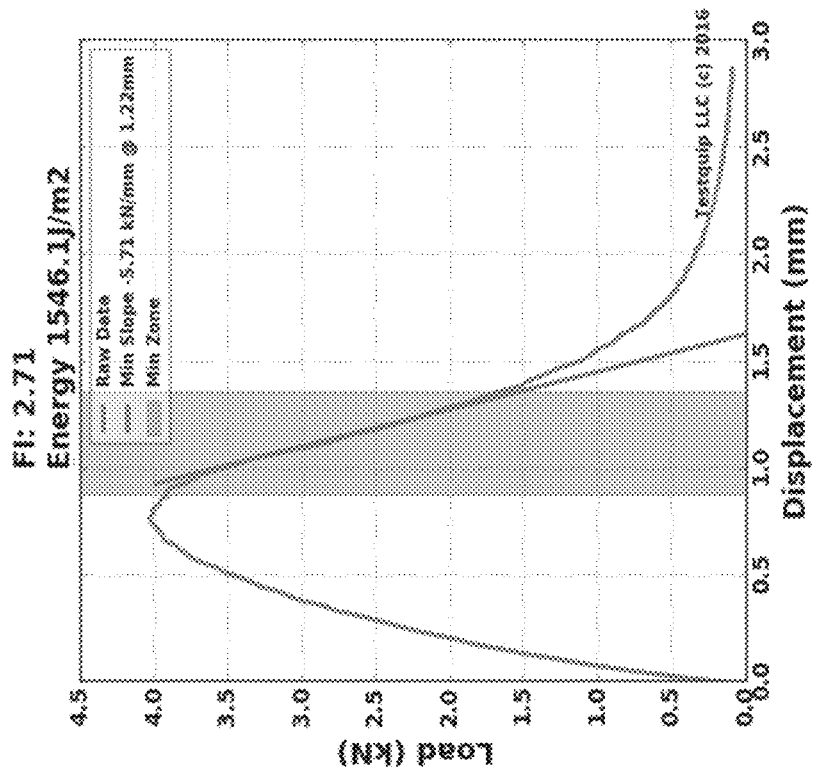
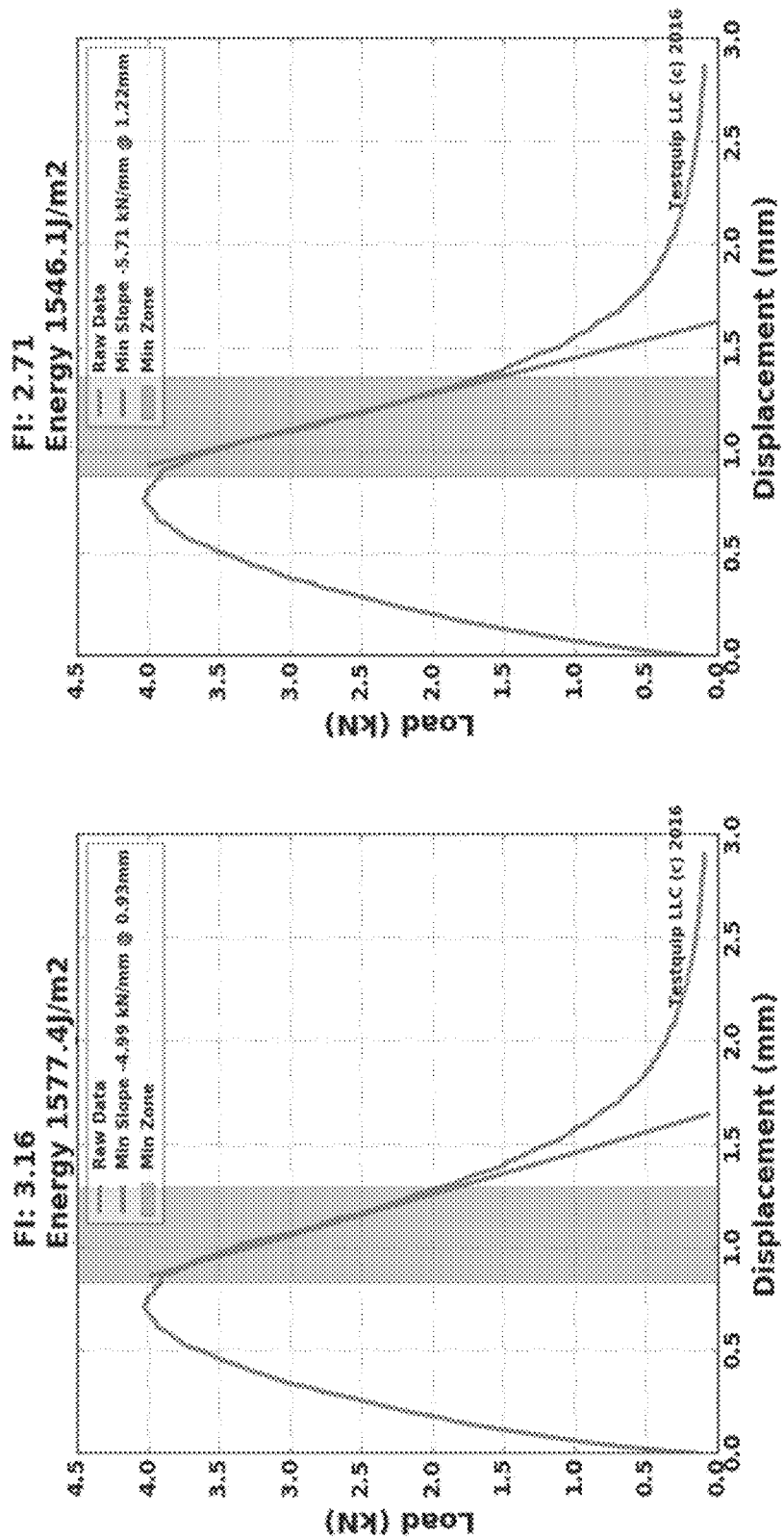
FIG. 9D
FIG. 9E

MATERIAL PERFORMANCE TESTING INCLUDING IMPROVED LOAD DETECTION

CROSS-REFERENCE TO RELATED APPLICATIONS

This application claims the benefit of U.S. Provisional Ser. No. 62/443,628 filed Jan. 6, 217. This disclosure of the prior application is considered part of (and is incorporated by reference in) the disclosure of this application.

TECHNICAL FIELD

This specification generally relates to systems, techniques, apparatuses, and devices for improved displacement control of loading apparatuses used for performance testing of constructions materials, such as asphalt, concrete, masonry, structural steel, soil, and others.

BACKGROUND

Testing protocols and control systems have been developed to test the fracture properties of asphalt. For example, Illinois Test Procedure 405 has been developed and published by the Illinois Department of Transportation for determining the fracture potential of asphalt mixtures using the Illinois Flexibility Index Test (I-FIT). As part of this test, an asphalt pavement core or Superpave Gyratory Compactor (SGC) compacted asphalt mixture specimen is trimmed and cut in half to create a semicircular shaped test specimen. A notch is sawn in the flat side of the semicircular specimen opposite the curved edge. The specimen is conditioned and maintained through testing at 25° C. (77° F.). The specimen is positioned in the fixture with the notched side down centered on two rollers. A load is applied along the vertical radius of the specimen and the loads and Load Line Displacement (LLD) are measured during the entire duration of the test. The load is applied such that a constant LLD rate of 50 mm/min is obtained and maintained for the duration of the test.

In a related standard, the American Association of Street Highway and Transportation Officials (AASHTO) AASHTO Designation TP 124-16 also describes the method of testing for determining the fracture potential of asphalt mixtures using semicircular bend geometry (SCB) at intermediate temperatures, similar to the I-FIT test.

SUMMARY

This document generally describes systems and control techniques for improved displacement control of loading apparatuses used for performance testing of materials, such as for the I-FIT and ASSHTO fracture potential tests. In particular, previous control systems and apparatuses have relied on the use of a singular LLD measurement device that is cantilevered off the side of the load head to provide LLD measurements, which are then used to control the LLD rate being applied to the specimen under test and to determine the ultimate flexibility index (FI) for the specimen. The FI measurement can indicate how well an asphalt specimen under test can carry a load after it has reached an initial structural breaking point. To provide accurate, consistent, and reliable FI measurements, a testing apparatus and control system needs to be able to accurately measure displacement of the load head and to account for deformation of the head during testing to ensure a consistent rate of LLD is applied to the specimen. Measurements being off by as much as $\frac{1}{1000}$" can cause the FI measurement to be incorrect by significant amounts—potentially providing false positives for failing specimens.

As described throughout this document, improved displacement control can be achieved in a variety of ways, such as through the use of multiple LLD measurement devices (e.g., multiple displacement transducers, other suitable LLD measurement devices) to provide multiple LLD measurements that can be combined to calculate a more accurate position and/or position rate (velocity) for the load head. Control of an actuator driving the load head can additionally be improved by using the more accurate position and/or position rate information, which can provide for more consistent and reliable LLD rate during testing, and ultimately more accurate and reliable FI measurements for the sample under test.

Multiple LLD measurements taken at the same time from multiple displacement transducers can be combined in any of a variety of ways, such as through averaging the values, using weighted averages (e.g., weighting based on any of a variety of factors), median values, and/or other combinations of values.

Multiple LLD measurement devices, such as multiple displacement transducers, can be located on opposing or near-opposing sides of a specimen under test so that bending moments in the load head (and/or other variations in the position of the LLD measurement devices not attributable to the deformation of the specimen under test and/or the load head) can be accounted for and discounted. Such positioning variations in a LLD measurement device can introduce errors that can dramatically alter the LLD rate and the ultimate FI measurement for a test if unaccounted for. For example, with a single cantilevered LLD measurement device off of one side of a specimen under test, prior apparatus and control systems (e.g., I-FIT test) may not be able to detect or correct for such positioning variations that are not attributable to the specimen under test or the load head, and may instead be interpreted as part of the LLD measurement for the specimen under test and/or the load head. The disclosed technology improves upon the accuracy of such control systems and apparatuses by accounting and correcting for such variations, which should not be attributed to either the specimen under test or the load head in order to ensure an accurate FI test result. For example, by combining measurements from multiple LLD measurement devices (e.g., using the average of multiple displacement transducers) from particularly selected reference points on a machine, the bias introduced by machine compliance can be cancelled, resulting in a more accurate measurement of displacement and loading rate control of the specimen under test.

In one implementation, a material testing apparatus includes an actuator to drive a piston according to electronic control signals; a load head to supply a load to a material specimen in a first dimension, wherein force is applied to the load head by the piston; a plurality of load line displacement (LLD) reference points that extend radially outward from the load head; a plurality of LLD measuring devices that correspond to the plurality of LLD reference points, each of the plurality of LLD measuring devices (i) being positioned to detect a position of a corresponding LLD reference point along the first dimension and (ii) being configured to transmit position signals to a controller; and a load cell to measure the load supplied to the material specimen by the load head, wherein the load cell is configured to transmit load signals to the controller.

Such material testing apparatus can optionally include one or more of the following features. The plurality of LLD measuring devices can include a plurality of transducers. The plurality of LLD reference points can include a plurality of magnets. The plurality of transducers can include a plurality of non-contact magneto restrictive position transducers that measure the positions of the plurality of magnets along the first dimension. The plurality of magnets can extend radially outward from the load head in a second dimension that is substantially perpendicular to the first dimension. The plurality of magnets can extend from opposing sides of the load head. The plurality of non-contact magneto restrictive position transducers can be positioned on opposing sides of the material specimen. The material specimen can be an asphalt specimen. The controller can be programmed to perform a flexibility index (FI) test on the asphalt specimen using feedback control based on (i) a combination of the position signals from the plurality of non-contact magneto restrictive position transducers and (ii) the load signal from the load cell. The controller can provide the control signals to the actuator according to the feedback control so that a target rate of LLD is achieved during the FI test. The target rate of LLD can be 50 mm/minute. The combination of the position signals can include an average of the position signals. The controller can be separate from the apparatus. The apparatus can further include the controller, wherein the controller is programmed to perform a performance test on the material specimen using feedback control based on (i) a combination of the position signals from the plurality of LLD measuring devices and (ii) the load signal from the load cell, and wherein the controller determines and provides the control signals to the actuator according to the feedback control so that a target rate of LLD is achieved during the performance test. The combination of position signals can include an average of the position signals.

In another implementation, a material testing system includes an actuator to drive a piston according to electronic control signals; a load head to supply a load to a material specimen in a first dimension, wherein force is applied to the load head by the piston; a plurality of load line displacement (LLD) reference points that extend radially outward from the load head; a plurality of LLD measuring devices that correspond to the plurality of LLD reference points, each of the plurality of LLD measuring devices (i) being positioned to detect a position of a corresponding LLD reference point along the first dimension and (ii) being configured to transmit position signals; a load cell to measure the load supplied to the material specimen by the load head, wherein the load cell is configured to transmit load signals; and a controller configured to (i) perform feedback control of the actuator based, at least in part, on the position signals and the load signals during a performance test of the material specimen, (ii) record data during the performance test, and (iii) determine a result for the performance test based on the recorded data.

Such a material testing system can optionally include one or more of the following features. The feedback control includes repeatedly performing the following during the performance test: receive the position signals from the plurality of LLD measuring devices, receive the load signals from the load cell, combine the position signals into a combined position, determine an LLD measurement for the material specimen based on the combined position, compare the LLD measurement with an target loading rate for the performance test, determine the control signals for the actuator based on the comparison and the load signals, and provide the control signals to the actuator. Combining the position signals can include averaging the position signals and the combined position can be an average position. The performance test can include an FI test. The material specimen can include an asphalt specimen. The data that is recorded can include the average position and the load signals. The result for the FI test can be an FI result value. The target loading rate can include 50 mm/minute. The plurality of LLD measuring devices can include a plurality of transducers. The plurality of LLD reference points can include a plurality of magnets. The plurality of transducers can include a plurality of non-contact magneto restrictive position transducers that measure the positions of the plurality of magnets along the first dimension. The plurality of magnets can extend radially outward from the load head in a second dimension that is substantially perpendicular to the first dimension. The plurality of magnets can extend from opposing sides of the load head. The plurality of non-contact magneto restrictive position transducers can be positioned on opposing sides of the material specimen. The material specimen can include an asphalt specimen. The controller can be programmed to perform a flexibility index (FI) test on the asphalt specimen using feedback control based on (i) a combination of the position signals from the plurality of non-contact magneto restrictive position transducers and (ii) the load signal from the load cell. The controller can provide the control signals to the actuator according to the feedback control so that a target rate of LLD is achieved during the FI test. The target rate of LLD can be 50 mm/minute. The combination of the position signals can include an average of the position signals. The plurality of LLD measuring devices can include two LLD measuring devices. The plurality of LLD measuring devices can include four LLD measuring devices.

In another implementation, a method for performing a performance test on a material specimen includes performing feedback control on a material testing apparatus that includes (i) a load head to supply a load to a material specimen, (ii) a plurality of load line displacement (LLD) reference points that extend radially outward from the load head, (iii) a plurality of LLD measuring devices to provide position signals indicating positions of the plurality of LLD reference points, and (iv) a load cell to provide load signals for the load supplied to the material specimen, the feedback control including repeatedly performing the following: receiving the position signals from the plurality of LLD measuring devices, receiving the load signals from the load cell, combining the position signals into a combined position, determining an LLD measurement for the material specimen based on the combined position, comparing the LLD measurement with an target loading rate for the performance test, determining the control signals for the actuator based on the comparison and the load signals, and providing the control signals to the actuator; and determining a result for the material specimen under the performance test based on, at least, changes in the combined position and the load signals during the performance test.

Certain implementations can provide one or more of the following advantages. For example, the disclosed technology can improve upon the accuracy, reliability, and consistency of FI tests that are performed on asphalt samples by reducing measurement error. Additional and/or alternative advantages are also possible, as described below.

BRIEF DESCRIPTION OF THE ATTACHMENTS

FIG. 1 is a conceptual diagram of an example control system for performing improved displacement control of an example loading apparatus for performance testing of a material specimen under test.

FIGS. 2A-B are simplified models of the example apparatus experiencing a bending moment while the specimen is under test.

FIG. 3 is a block diagram of an example feedback control system for a machine the uses a combination of multiple displacement measuring devices to control and measure the displacement rate of an actuator that is used to apply load to a specimen under test.

FIGS. 4A-F are varied views of the example apparatus depicted with multiple transducers to provide improved material test results.

FIGS. 5A-C present varied views of another apparatus with multiple transducer to provide improved material test results.

FIG. 6 is a graph with example FI test results using the example control systems and apparatuses.

FIGS. 7A-C are graphs of example FI test results using the example control systems and apparatuses.

FIGS. 9A-E depict an example comparison of average LLD measurements versus a stroke displacement measurement.

Figure 10:
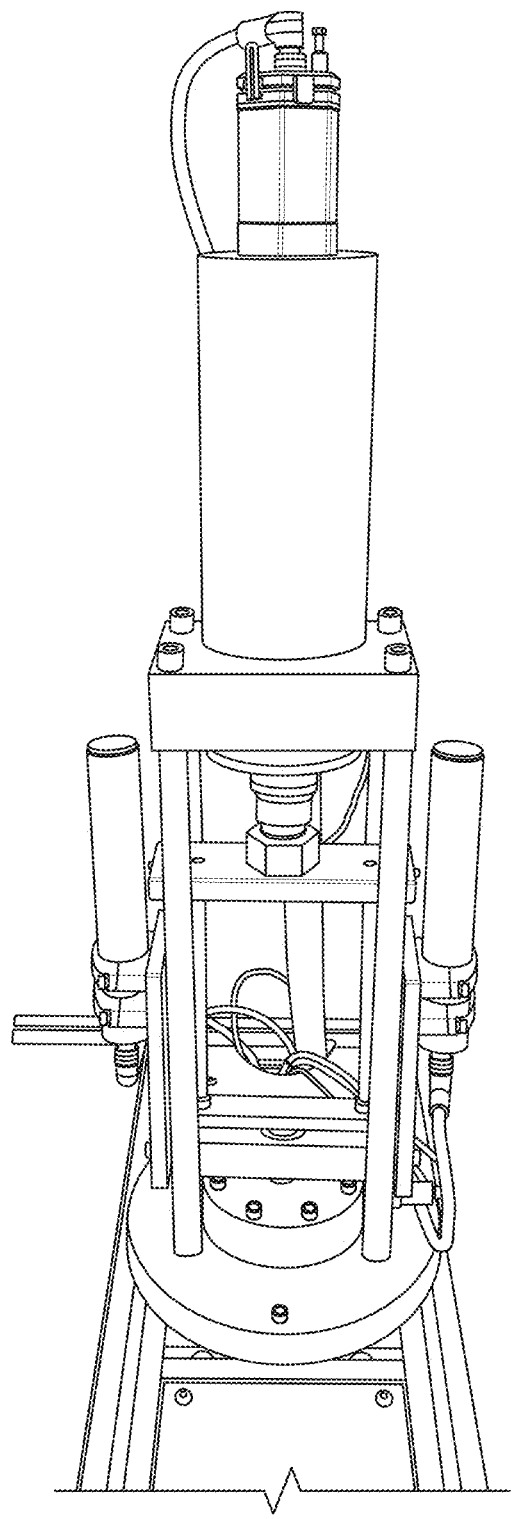

FIG. 10 is a photograph of another material testing apparatus that can use multiple displacement measuring devices for the load head to control testing in a feedback loop and to additionally provide improved testing results.

Figure 11:
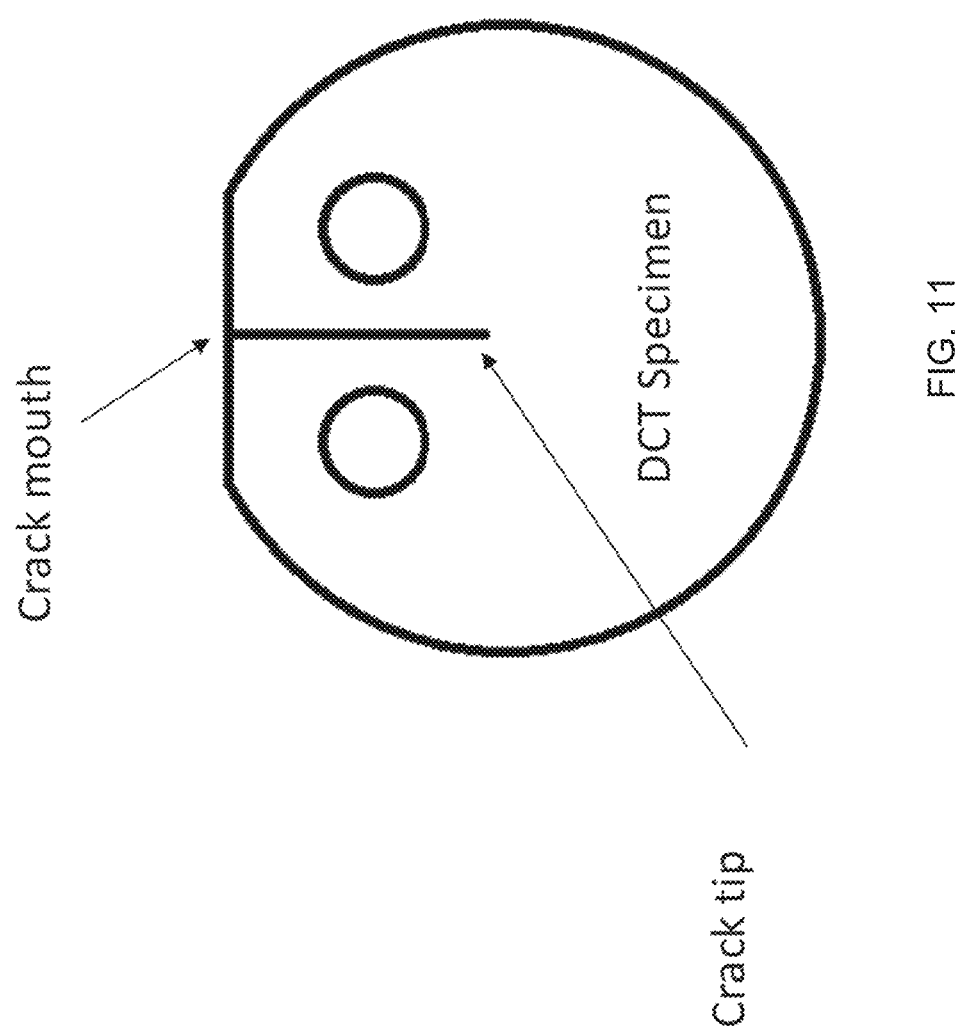

FIG. 11 is a side view of an example DCT test specimen.

Like reference numbers and designations in the various drawings indicate like elements.

DETAILED DESCRIPTION

Figure 1:
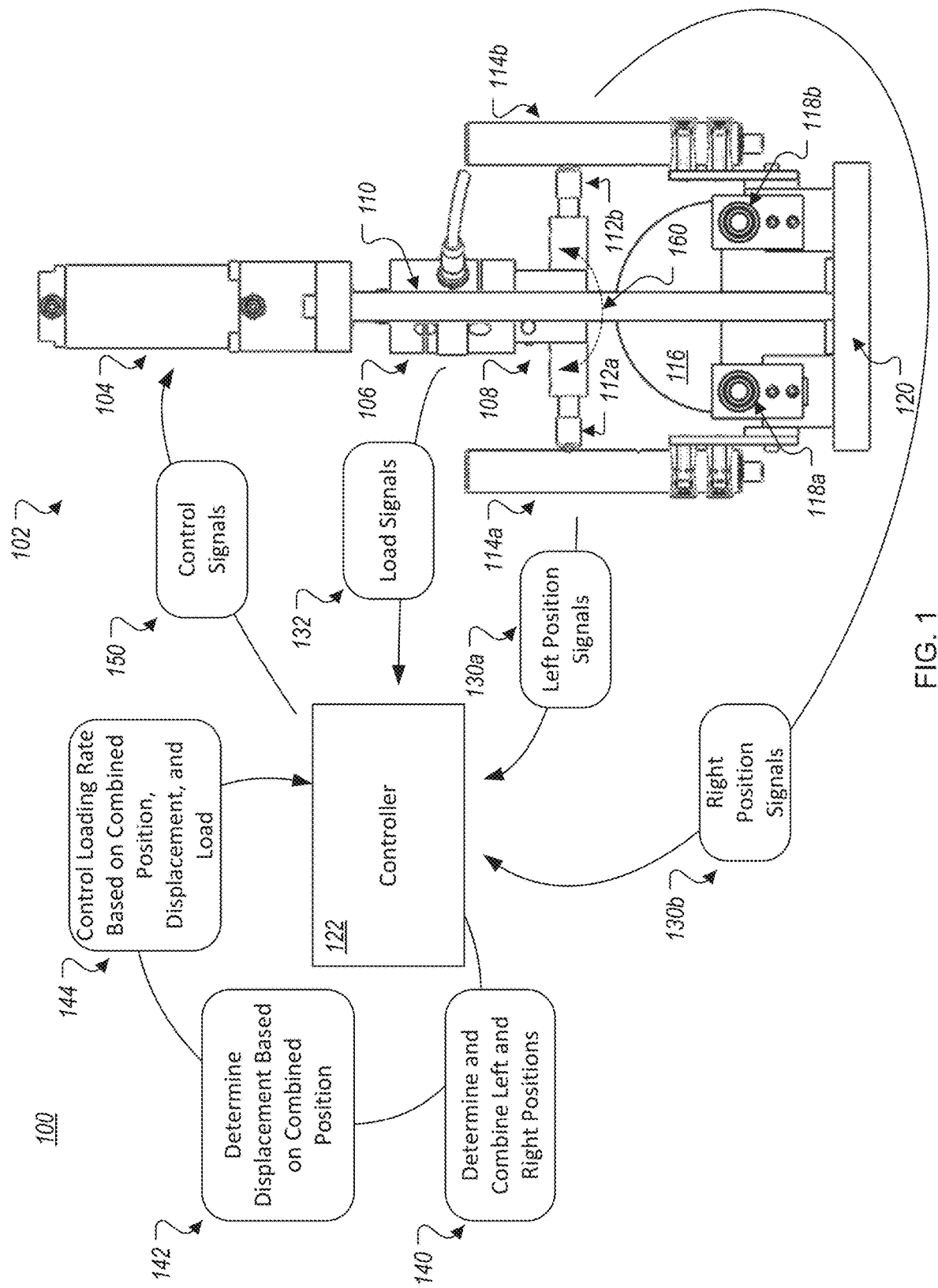

FIG. 1 is a conceptual diagram of an example control system 100 for performing improved displacement control of an example loading apparatus 102 for performance testing a material specimen 116 under test. In the depicted example, the apparatus 102 is performing a test on a SCB specimen 116, which is a semi-circular shape or half-disk of a material, such as an asphalt mixture. The apparatus 102 is designed to apply a load via a load head 108 to the specimen 116, which can be loaded in a three point bend configuration, for example. The load is applied by an actuator 104 (e.g., hydraulic actuator) which can drive the load head 108 along a load column 110 onto the specimen 116. For example, the top loading head 108 can use a pivoting rounded loading strip to contact the middle of the specimen 116, and force can be applied using a hydraulic actuator (example of actuator 104).

The apparatus 102 includes sensors to provide feedback signals to a controller 122 that is controlling application of the actuator 104 to provide, for example, a target LLD rate to the specimen 116 (e.g., driving the load head 108 at a target LLD rate of 50 mm/min). These sensors can include, for example, a load cell 106 to measure the load that is being applied to the specimen 116 and multiple transducers 114a-b (example LLD measuring devices) to provide measurements of the LLD. The transducers 114a-b measure the position of LLD reference points that are defined by reference point devices 112a-b (e.g., magnets) that are cantilevered off either side of the load head 108. For example, the transducers 112a-b can be non-contact magneto restrictive position sensors/transducers that measure the position of magnets (example reference point devices 112a-b) on the left and right side of the loading fixture 108. In another example, the transducers 112a-b can be contact-type LVDTs (or other contact-type transducers) that can physical contacted by physical objects (example reference point devices 112a-b) and/or can be placed directly on the specimen 116 to measure displacement (instead of or in addition to using reference points 112a-b). In this example, by averaging multiple contact-type sensors on the specimen 116, a high level of rate controllability and measurement can be achieved. Other types of position sensors can be used to directly measure on the specimen 116, such as extensometers (a type of reusable strain gauge). In a further example, other types of sensors (e.g., optical sensors, radiation sensors, vibration sensors, movement sensors, altimeters) can be used as the transducers 112a-b and corresponding position indicators (e.g., light sources, radiation sources) can be used as the reference point devices 112a-b, where appropriate.

As the load is being applied to the specimen 116, the load cell 106 can transmit load signals 132 to the controller 122, and the transducers 114a-b can transmit left and right position signals 130a-b to the controller 122. The controller 122, which can be any of a variety of appropriate computing devices (e.g., embedded controller, application-specific integrated circuit (ASIC), laptop/desktop computer, mobile computing device) that are configured to receive the signals 130a-b and 132, and to control the apparatus 102, can receive the signals and use them to determine the left and right positions for the head 108, and to combine the determined left and right positions (140). For example, the head 108 may have a bending moment 160 that may cause the head to pivot to the left or to the right. When this happens, each of the positions by themselves may inaccurately provide the displacement of the loading head 108. However, by combining the positions, the inaccuracies of each position can be canceled out to provide an accurate displacement for the head 108. In prior systems that used just a single transducer, such inaccuracies would not be recognized or eliminated from the head 108 displacement determination. The left and right positions can be combined in any of a variety of ways, such as through averaging, weighted averaging, determining the median value, and/or other appropriate techniques for statistically combining values.

Using the combined position information, the controller 112 can determine the displacement (e.g., LLD) for the head 108 and/or the specimen 116 (142), and can control the loading rate based on the combined position, the determined displacement, and/or the load measurement from the load cell 106. The loading rate can be determined so that the LLD rate is consistent and within an acceptable threshold of a target LLD rate (e.g., 50 mm/min). Control signals 150 can be transmitted to the actuator 104 by the controller 122. The steps 140-142 can be continually and repeatedly performed by the controller 122 to consistently control the loading rate for the sample 116 during the test.

The controller 122 can additionally record the displacement and load values over time during application of the test in order to calculate the results for the specimen 116. For example, the controller 122 can determine the FI for the specimen 116 by analyzing the displacement and load over time.

Figure 2A:
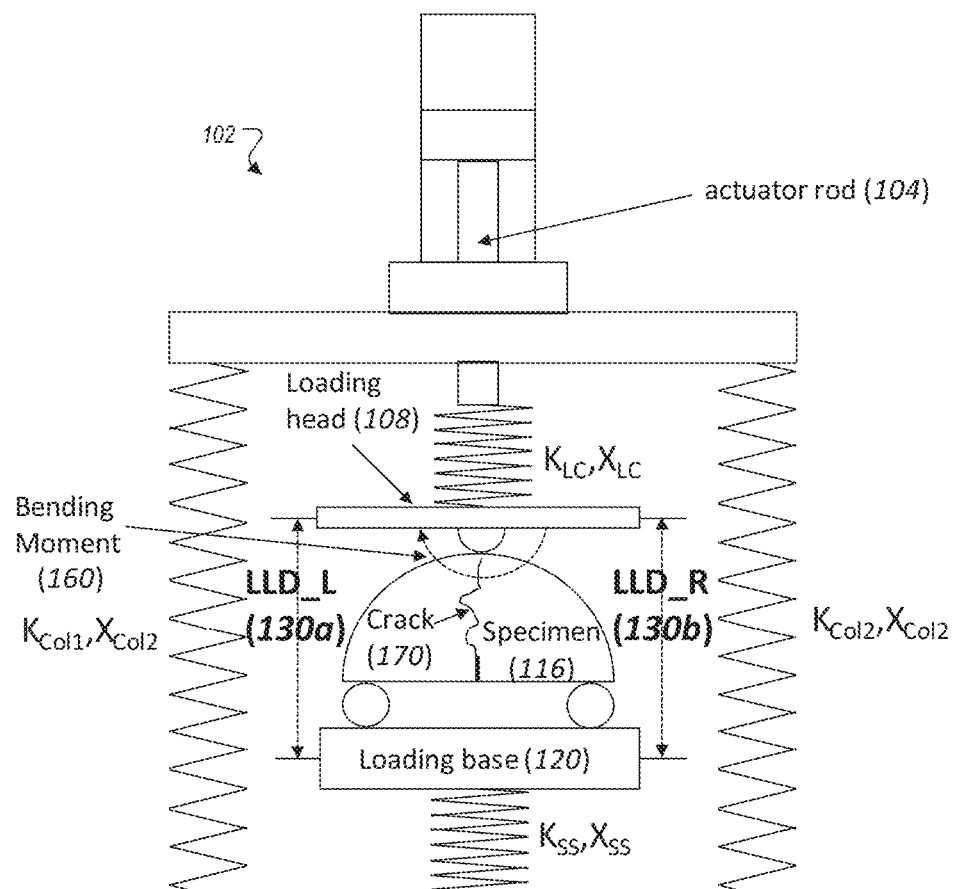
Figure 2B:
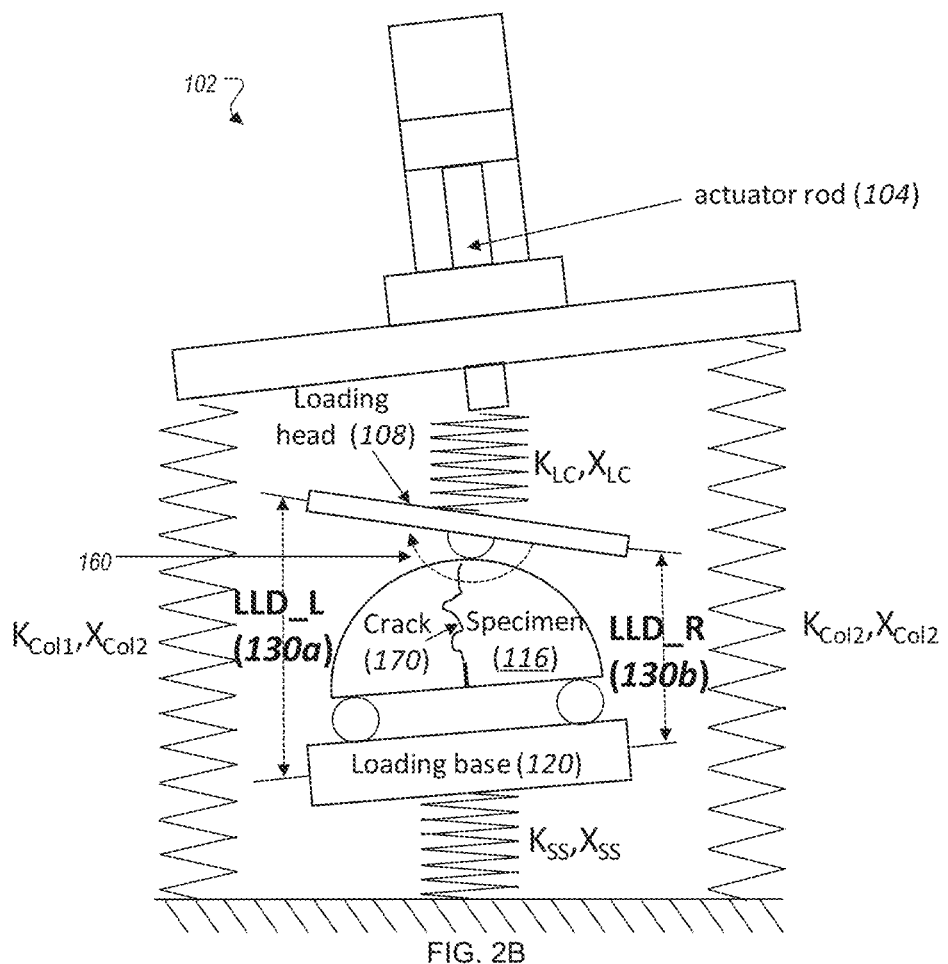

FIGS. 2A-B are simplified models of the example apparatus 102 experiencing a bending moment 160 while the specimen 116 is under test.

Referring to FIG. 2A, in the depicted example model the two loading columns and the single load cell are represented by springs. In some cases, a loading base 120 is supported a support shaft (or load cell), which can also be represented by a spring. The spring stiffness of load Col1 and Col2 are indicated by the $K_{Col1}$ and $K_{Col2}$, respectively. The load cell and support shaft stiffness is represented by $K_{LC}$ and $K_{SS}$, respectively. As the specimen is loaded, the loading columns, load cell, and support shaft all deflect by a value proportional to their stiffness. The amount of deflection is represented by the value X for each component.

In this example, the deformation of the specimen 160 (as indicated by the crack 170) is estimated by the relative difference between a reference point on the loading head 108 and loading base 120, referred to here as Load Line Displacement (LLD). When a bending moment 160 is induced on the loading head and loading base, the magnitude of the left side displacement (LLD_L, 130a) will not be the same as the displacement of the right side displacement (LLD_R, 130b). Accordingly, if only one of the LLD_L (130a) or LLD_R (130b) values were used by the controller 122, the ultimate FI results determined by the controller 122 would be different and inaccurate. By including devices 114a-b to measure both LLD_L and LLD_R, the controller 122 can account for the differing magnitude on the left and right sides to more accurately and consistently determine the LLD, and to more accurately determine the ultimate FI results for the specimen 116.

Referring now to FIG. 2B, this model shows the exaggerated compliance of the two loading columns, single load cell, and support shaft (as compared with the model in FIG. 2A). The deflection of the loading columns, load cell, and support shaft is not always uniform or predictable. Since the crack 170 is not uniform, as the specimen 116 breaks, a moment 160 (bending force) is induced on the loading frame components. This means that Col1 can deflect a different amount than Col2, and the loading head 108 and/or loading base 120 can compress and pivot. Using any of these elements as reference points in the estimation of the specimen 116 deformation can be introduce measurement bias. As shown in this example the displacements of LLD_L (130a) and LLD_R (130b) are not equal. Variation can additionally be introduced through different loading frames and fixtures that have different stiffness, and different components that deflect differently under load. Therefore, to reduce variability in the test results, the apparatus 102 can be equipped with multiple transducers 114a-b and the controller 122 can be programmed to combine multiple position measurements in order to mitigate the effects of frame and fixture compliance. For example, using average displacement control by the controller 122 can provide a cancelling effect of side measurement bias from averaging opposite (in the case of 2 transducers) or multiple (more than 2 transducers) sides of the loading fixture.

Figure 3:
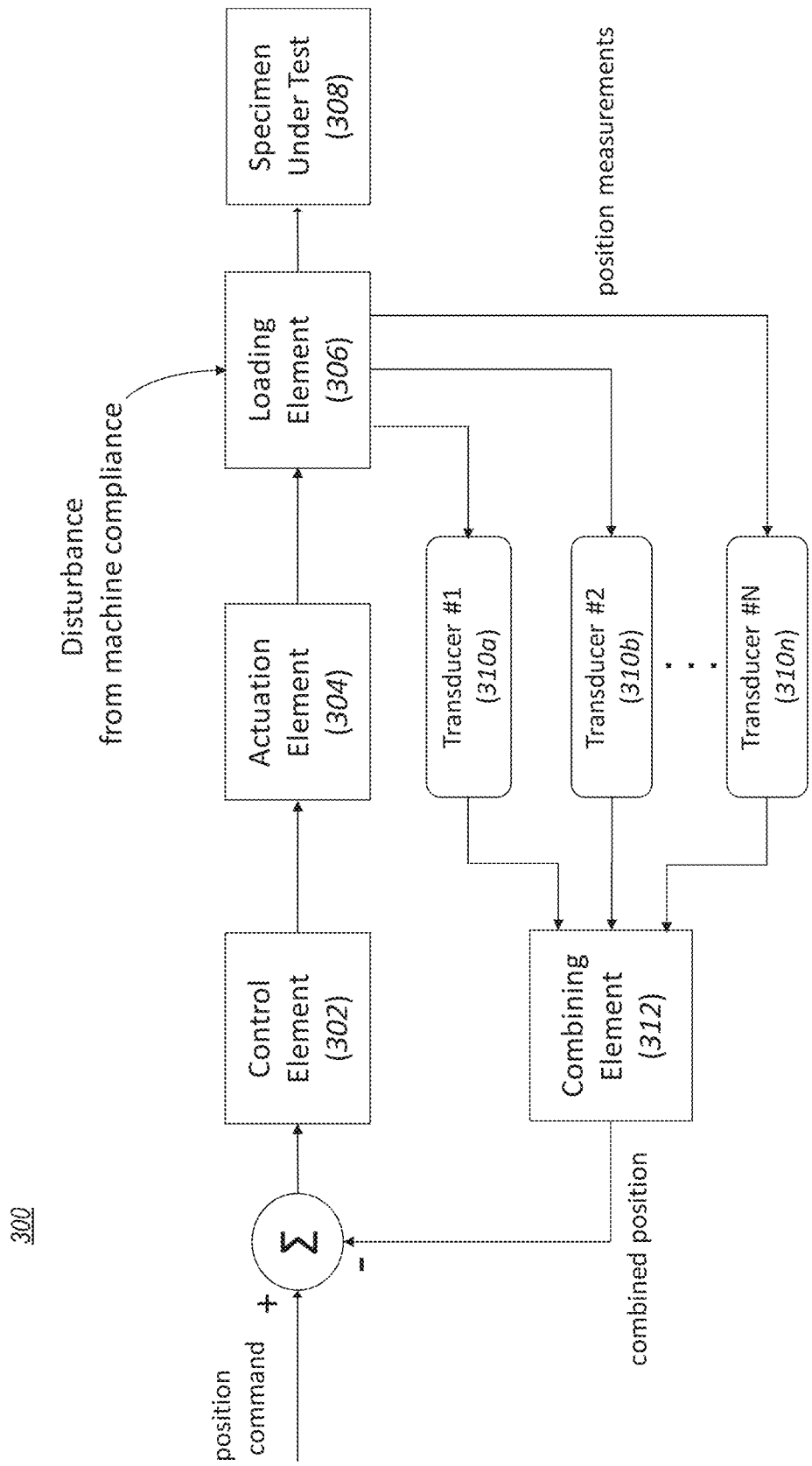

FIG. 3 is a block diagram of an example feedback control system 300 for a machine (e.g., apparatus 102) the uses a combination of multiple displacement measuring devices (e.g., transducers) to control and measure the displacement rate of an actuator that is used to apply load to a specimen under test. The system 300 applies to the control of position and/or position rate (using differentiated position).

The system 300 includes an example control element 302, such as an embedded digital controller, that runs a real-time operating system. The control element 302 can include, for example, PC hardware (e.g., processor, microprocessor, memory) that is part of the embedded controller and that is responsible for running the control algorithms, data acquisition, and signal outputs in both digital and analog form. For example, the controller 122 is one example of the control element 302.

The system 300 also includes an actuation element 304 that can create linear motion for a loading head. The actuation element 304 can be, for example, a hydraulic actuator, such as the actuator 104. Movement of a hydraulic actuator can be fed, for example, by a hydraulic pump through a hydraulic servo-valve (a flow control device). Other implementations of the actuation element 304 are also possible, such as mechanical screw drives and/or other load driving devices.

The actuation element 304 drives a loading element 306, which can include a loading frame and specialized fixtures for each specific test. For example, the loading element 306 can include a loading head (e.g., loading head 108) attached to the end of the piston rod (through a load cell). The hydraulic cylinder can be held in place through load columns (e.g., 2 columns, 4 columns) attached to a top crossmember and bottom base plate. The base of the loading fixture can include additional points of contact with the specimen under test (e.g., specimen 116). Other configurations of the loading element 306 are also possible.

The loading element 306, however, can be susceptible to disturbances, which are errors resulting from machine compliance that includes, but not limited to, stretching of the loading columns, compression of the load cell, compression of the hydraulic piston seals, bending of the fixture caused by non-uniform breaking of the specimen under test, and/or combinations thereof. Each element of the loading fixture can be thought of as a spring with different stiffness. In fact, a load cell can be, by definition, a spring device. Since each machine can have a different stiffness, each machine can have a different magnitude of measurement and control error. The systems 100 and 300 can eliminate the uncertainty caused by such disturbances through control and measurement techniques that leverage multiple position measurements to cancel the effects of errors by combining (e.g., averaging) the multiple measurements to mitigate the effect of such disturbances.

The loading element 306 can apply the load to a specimen under test 308, which can be an asphalt sample, which is a viscoelastic material. Viscoelastic materials have a unique property in which the stiffness of the material is a function of the displacement rate.

Position measurements can be determined for the system 300 by multiple transducers 310a-n, which can include any number of transducers measuring position at independent locations relative the specimen under test 308 (e.g., measuring on opposing sides of the specimen 308). The transducers 310a-n can measure the position of elements (e.g., reference point magnets) that extend from the loading element 306 (e.g., extend perpendicular to the direction of linear displacement). The position elements can be configured so that they provide readily comparable position measurement values, such as through extending the same or similar distance from a common point (e.g., center point) on the loading element 306. The transducers 310a-n can be, for example, non-contact type, magneto restrictive position sensor, such as BALLUFF, model BTL001 W. Other possible transducers 310a-n can include any form of linear variable differential transformer (LVDT). Types of LVDTs can include contact type and/or non-contact type transducers. In another example, a rotary variable differential transformer (RVDT)/motor encoder typically used on a mechanical screw type actuator could additionally and/or alternatively be used.

The position measurements from the transducers 310a-n can be provided to a combining element 312, which can be, for example, a routine on a controller (e.g., software on embedded controller) that combines the signals (e.g., averages the signals) and maps the combined position to its own unique feedback channel that is used by the control element 302. The feedback control loop including the control element 302, the actuation element 304, the loading element 306, the transducers 310a-n, and the combining element 312 can be used to continually control the loading rate applied to the specimen 308 so that a target rate is achieved, and to record displacement and loading measurements to determine an ultimate test result for the specimen 308 (e.g., FI test result).

Figure 4A:
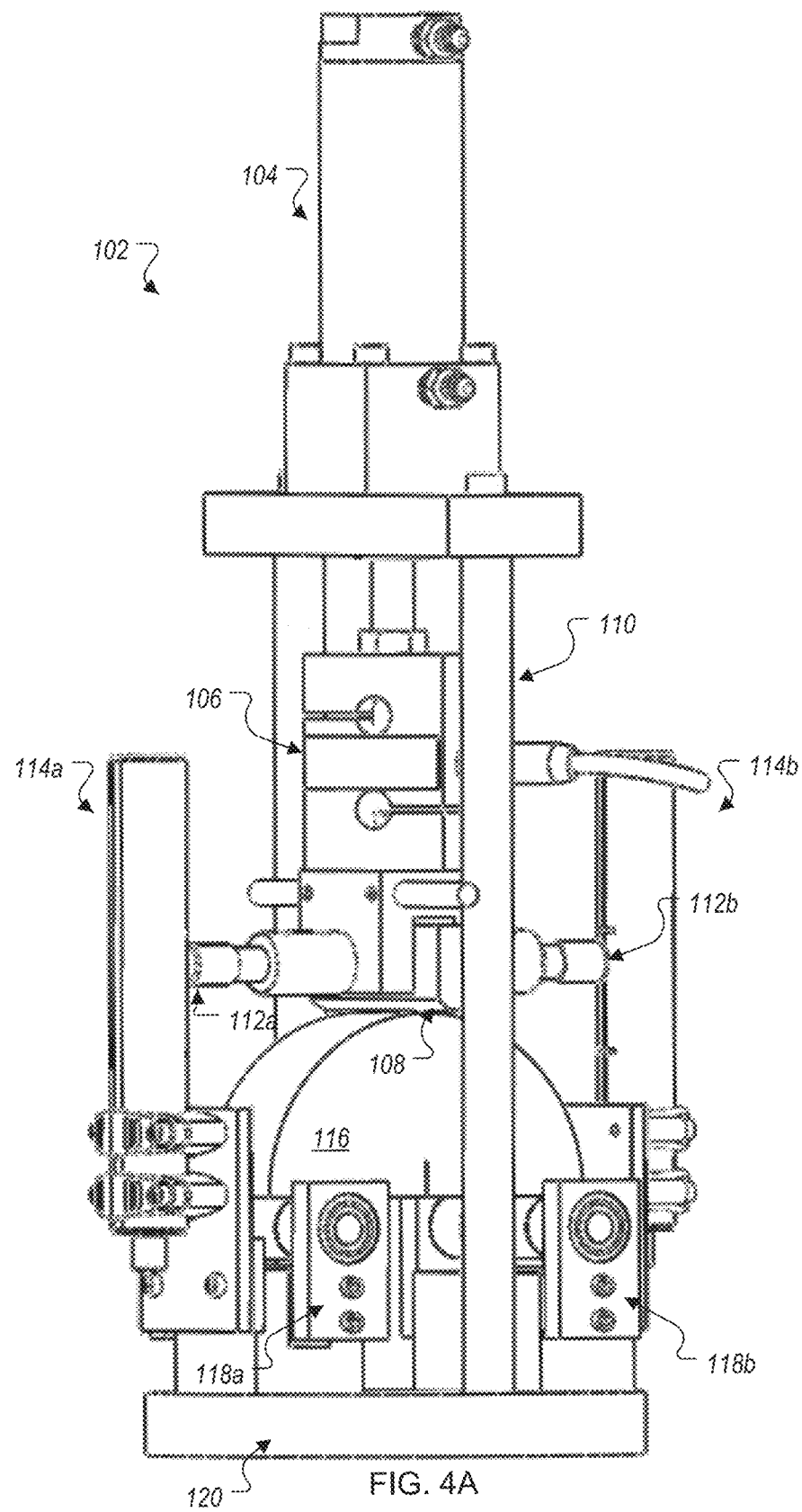
Figure 4B:
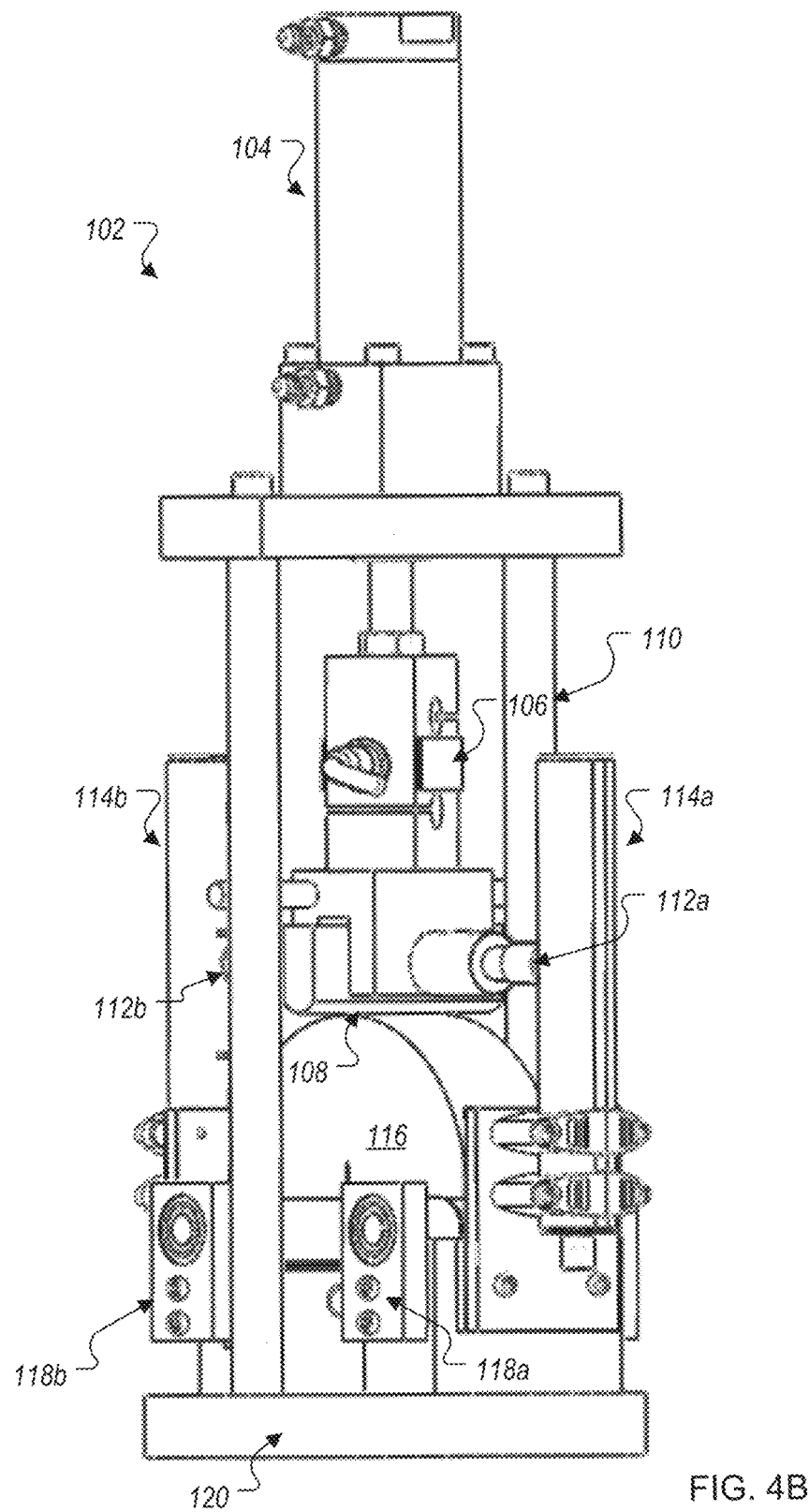
Figure 4C:
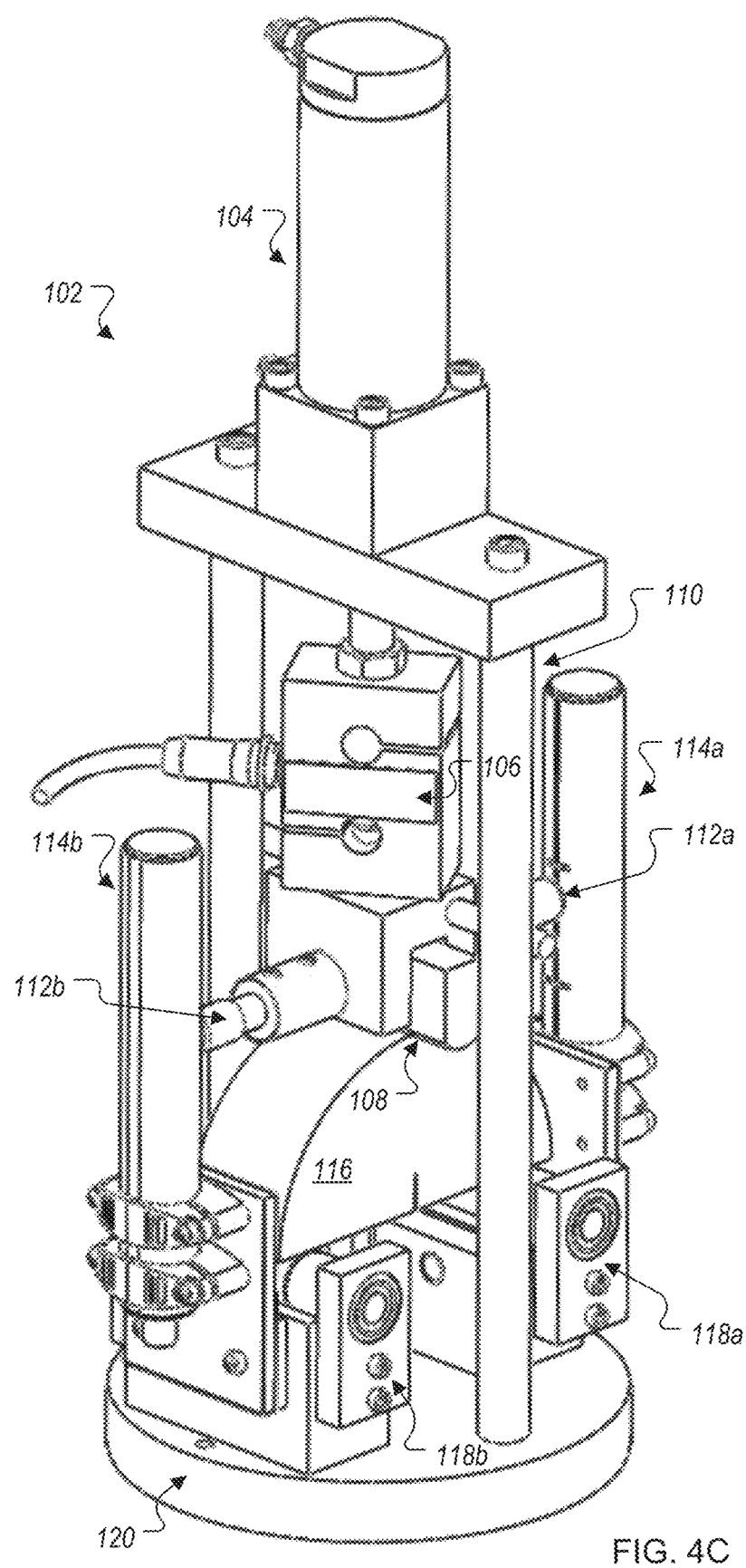
Figure 4D:
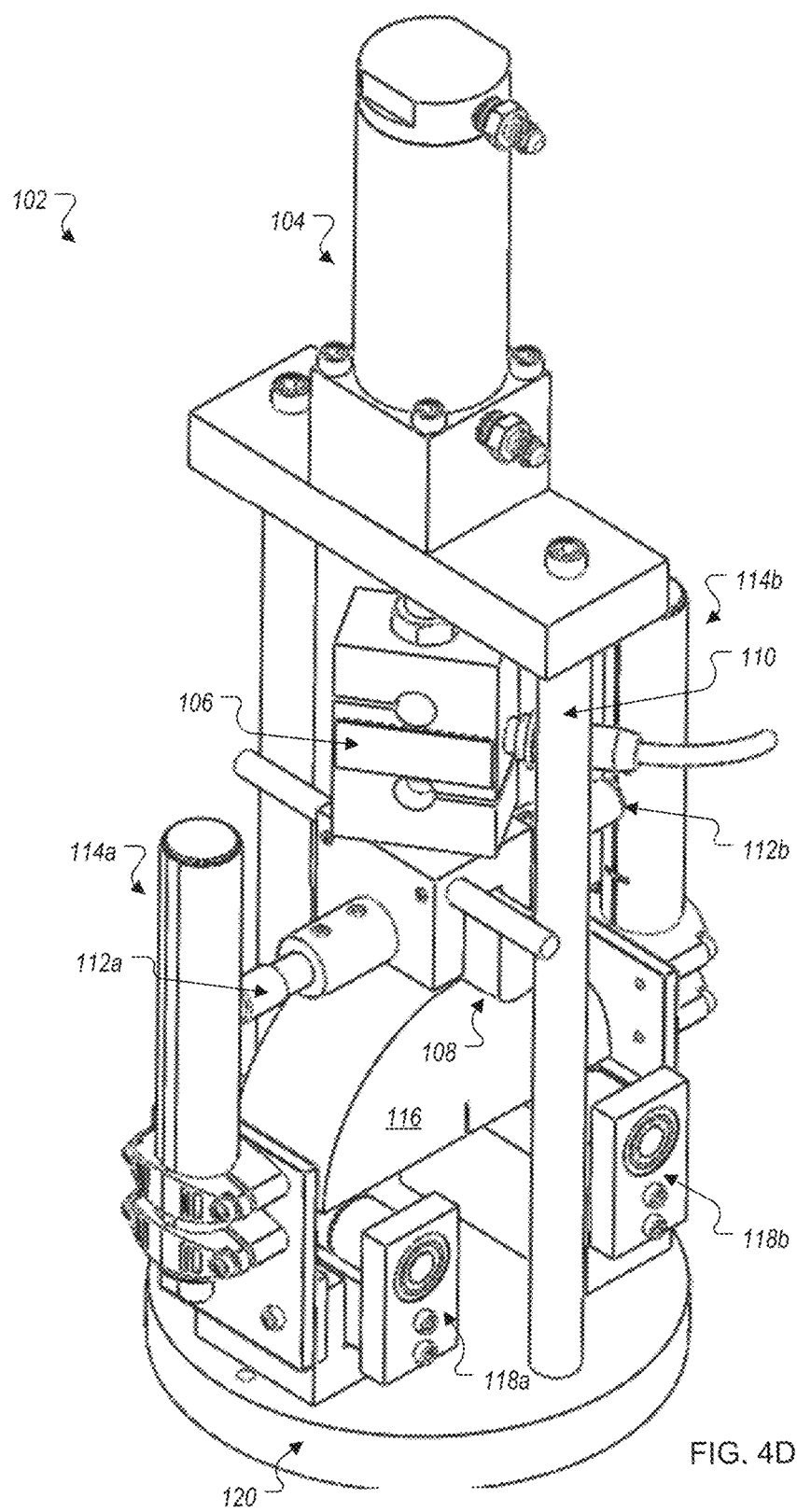
Figure 4E:
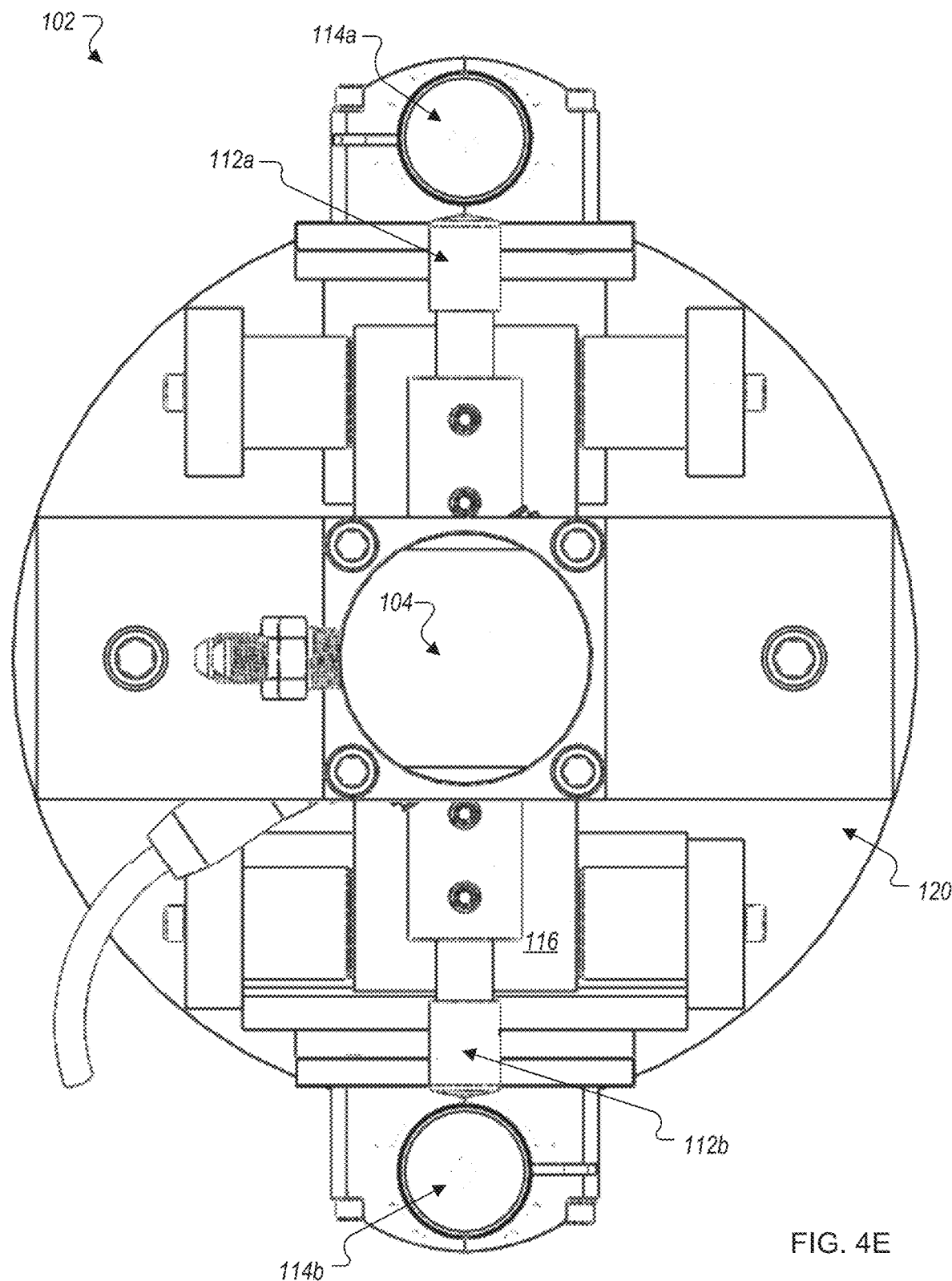
Figure 4F:
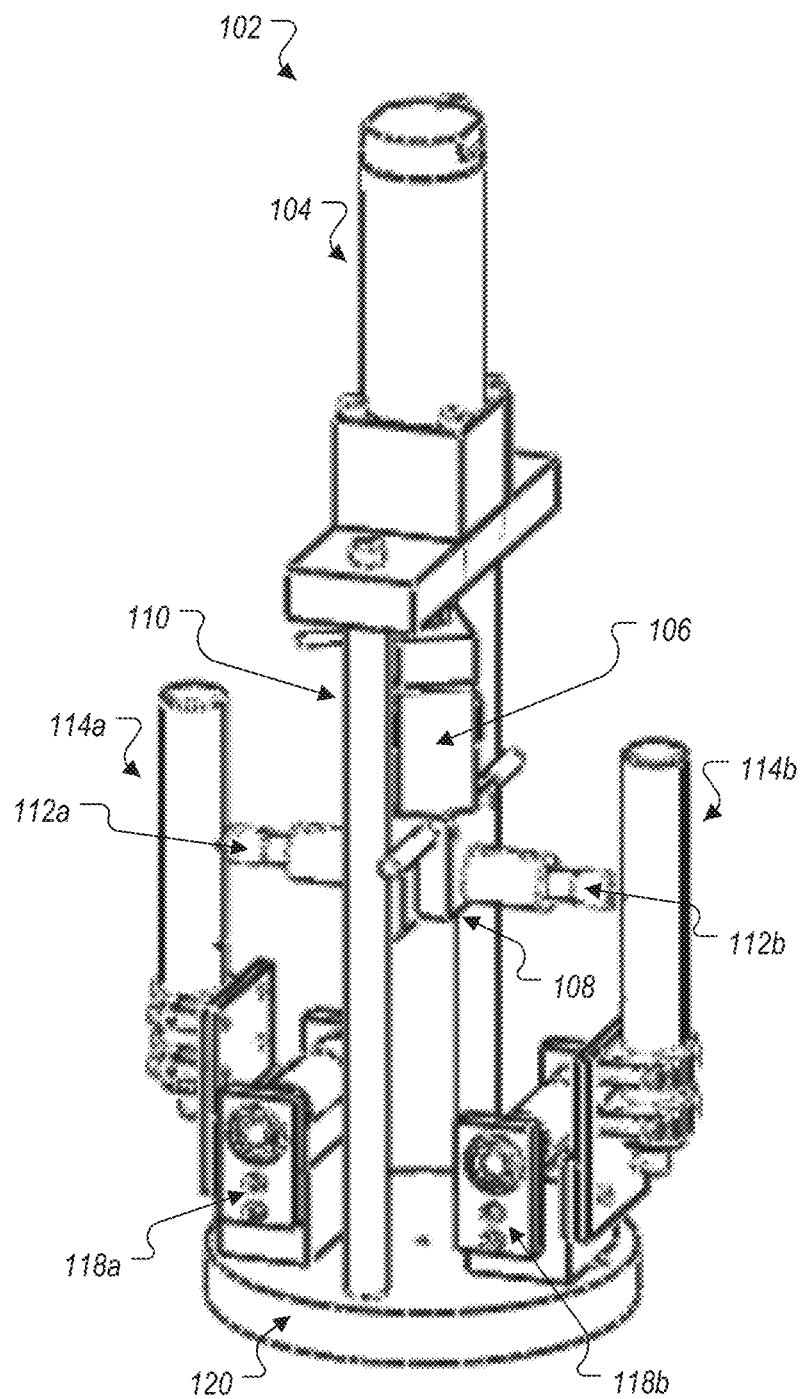

FIGS. 4A-F are varied views of the example apparatus 102 depicted in FIG. 1 with multiple transducers 114a-b to provide improved material test results. FIG. 1 presents a front view of the apparatus 102. FIGS. 4A-B present angled views of the apparatus 102. FIGS. 4C-D present varied perspective views of the apparatus 102. FIG. 4E presents a top view of the apparatus 102. FIG. 4F presents a perspective view of the apparatus 102 without the specimen 116.

Figure 5A:
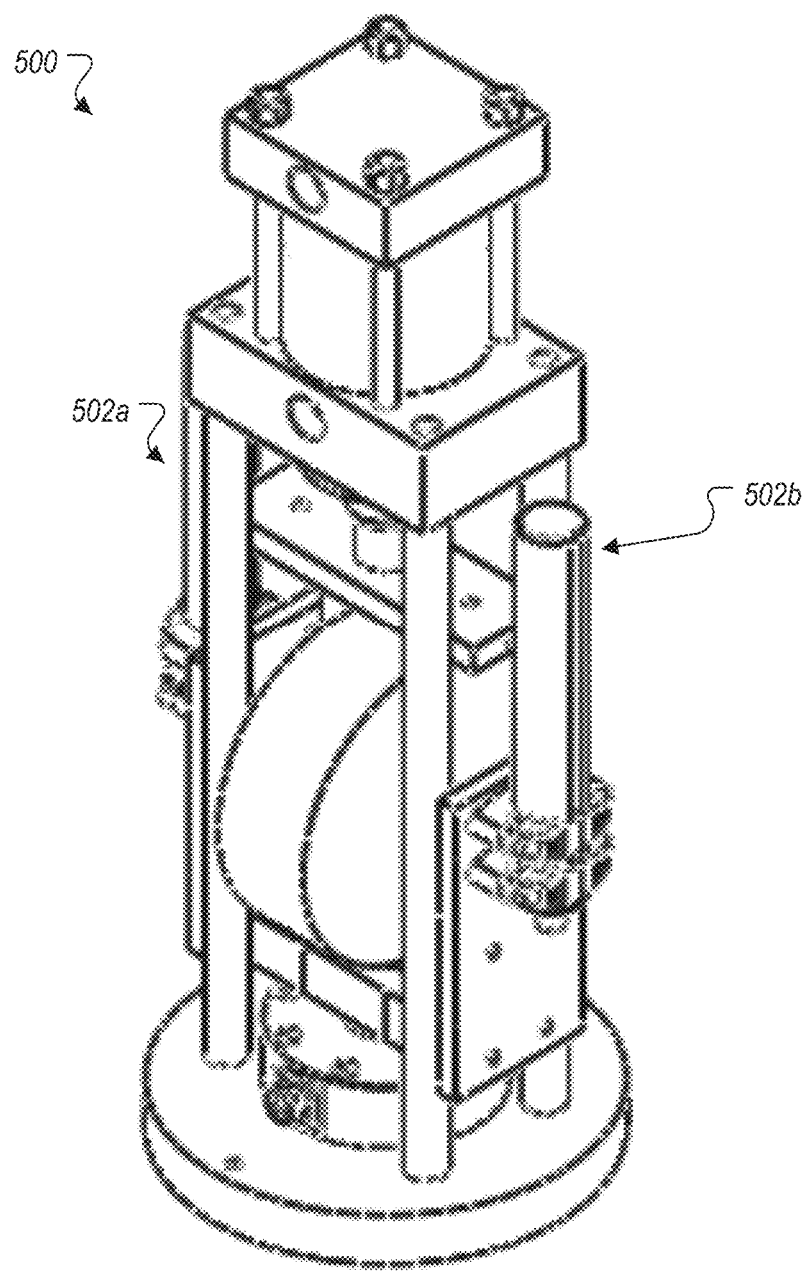
Figure 5B:
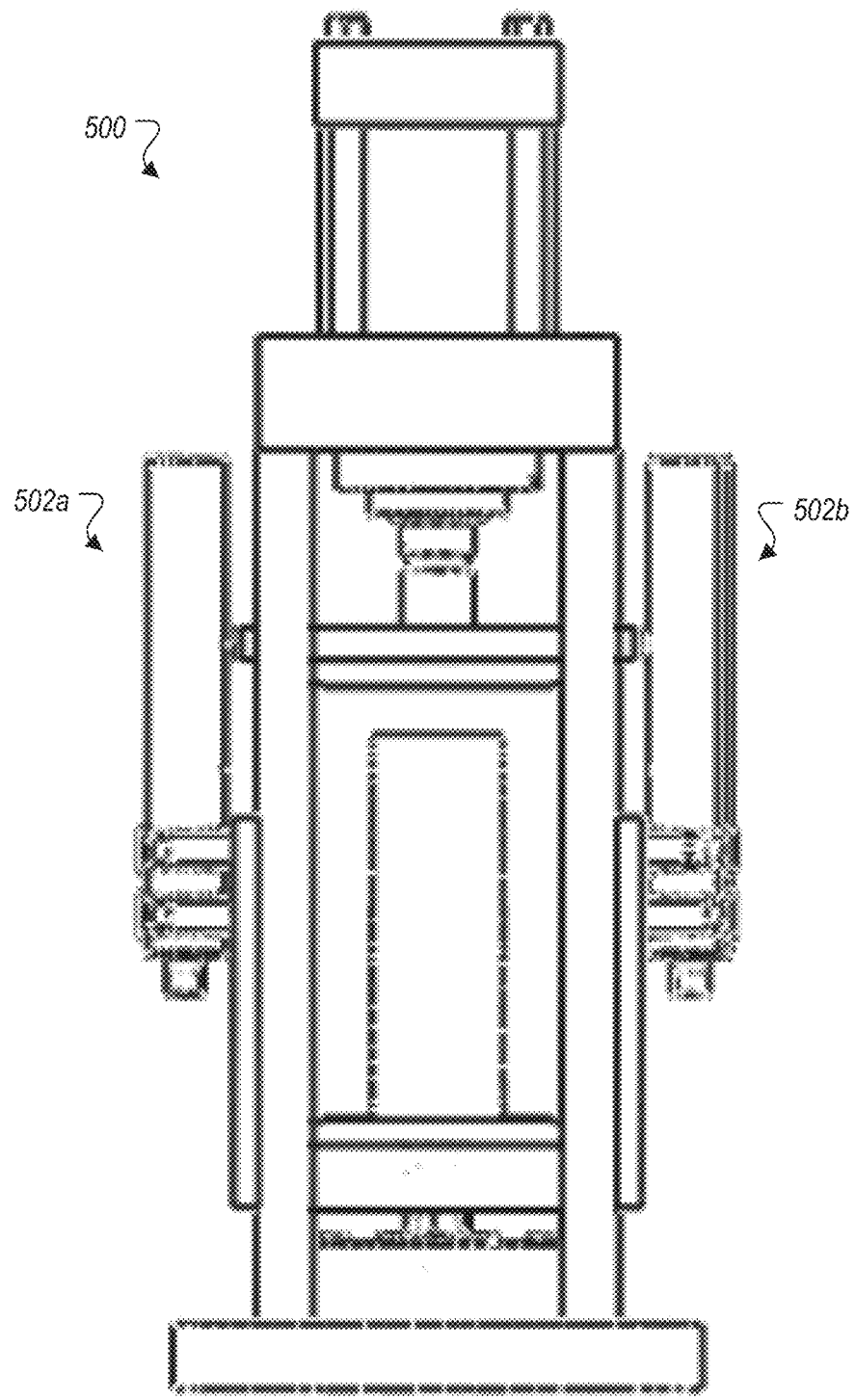
Figure 5C:
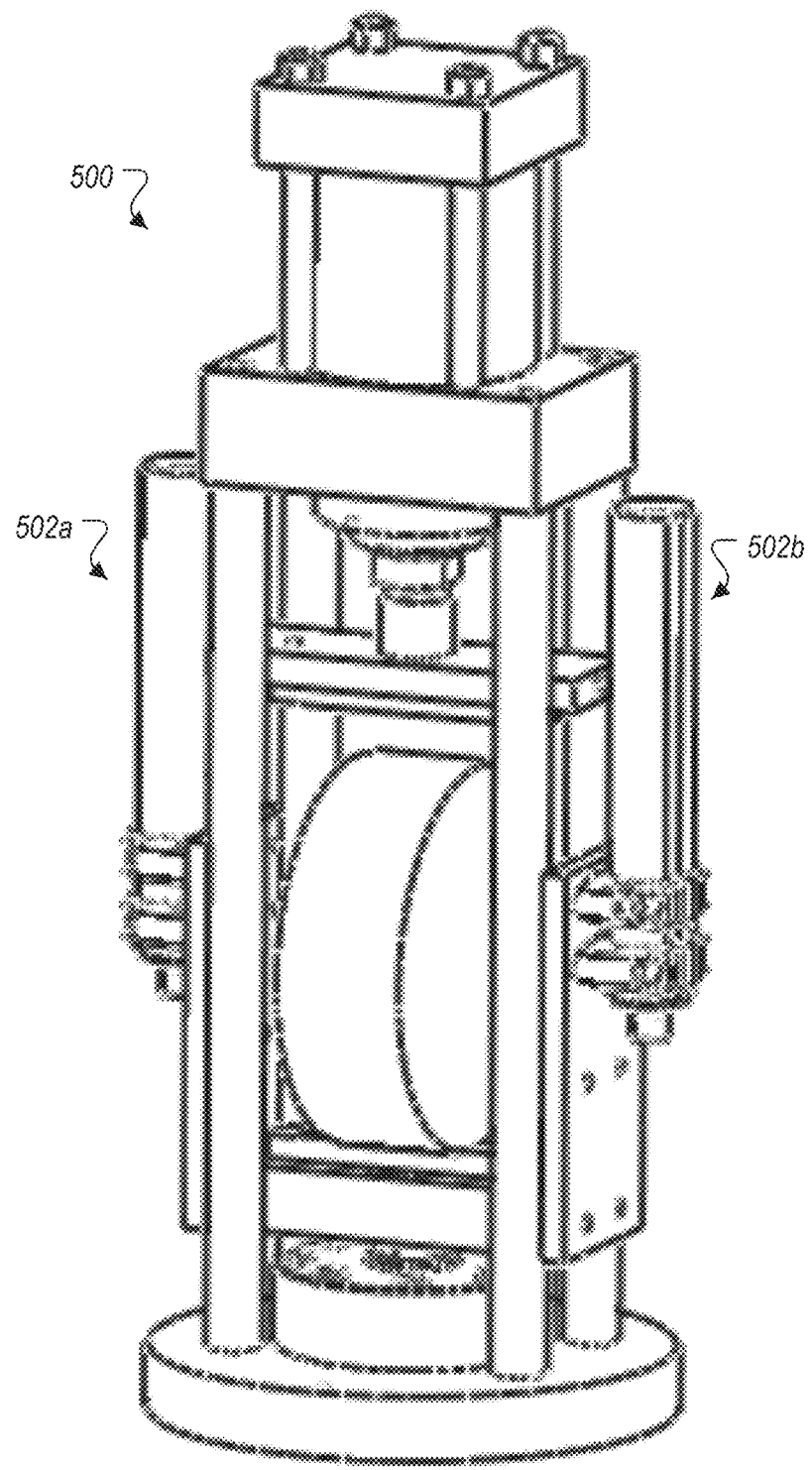

FIGS. 5A-C present varied views of another apparatus 500 with multiple transducer 502a-b to provide improved material test results. In the depicted examples, the apparatus 500 is configured to perform tests on circular material samples, such as asphalt. The apparatus 500 can be used in combination with a controller to perform improved material testing, as described above with regard to FIGS. 1-4. FIG. 5A presents a perspective view of the apparatus 500. FIG. 5B presents a front view of the apparatus 500. FIG. 5C presents another perspective view of the apparatus 500. As described below with regard to FIG. 10, the apparatus 500 can be used to perform indirect tension testing (IDT).

Figure 6:
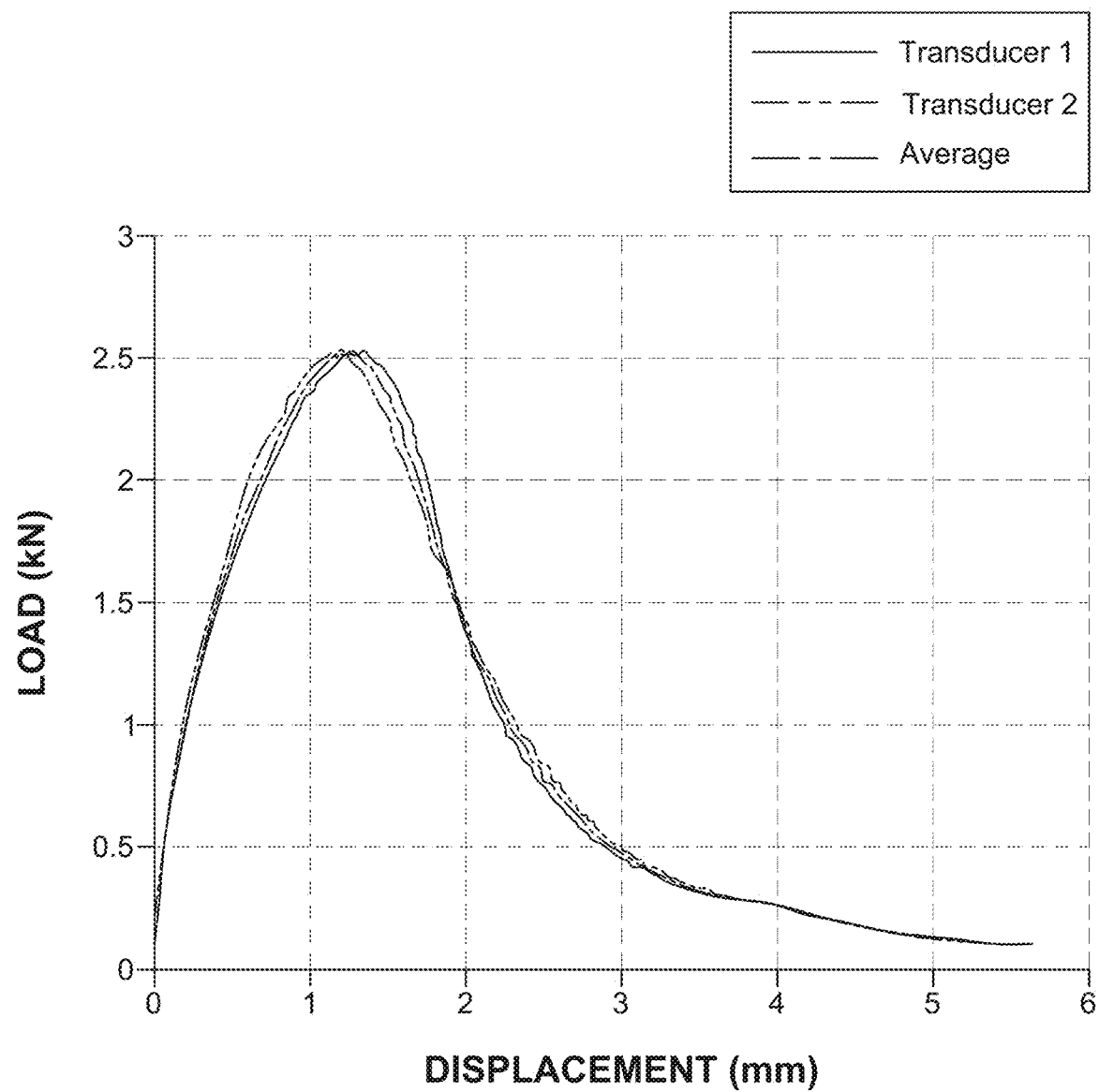

FIG. 6 is a graph with example FI test results using the example control systems and apparatuses described above with regard to FIGS. 1-5. This example shows variability between transducer 1 and transducer 2. In this case, transducer 1 was mounted on the "left" side of the machine and transducer 2 was mounted on the "right" side of the machine. The average displacement (example combined displacement) is a better representation of the actual displacement of the specimen through the specimen centerline.

By using the average displacement to control the test, more accurate and better control of the specimen displacement rate can be achieved. For example, the desired target displacement rate can be 50 mm/min. In this example, the displacement rate for transducer 1 was 49.54 mm/min and the displacement rate for transducer 2 was 59.54 mm/min. However, using the average displacement to control actuation of the load, a better and more accurate rate of 50.04 mm/min was achieved—much closer to the target rate of 50 mm/min. Since the example FI test depicted uses displacement rate as a means to simulate temperature (using the concept of time-temperature superposition for viscoelastic materials), accurate and consistent rate control is as equally important as temperature control to providing reliable and consistent test results. Variability in rate (as well as temperature) can lead to variability in test results.

Figure 7A:
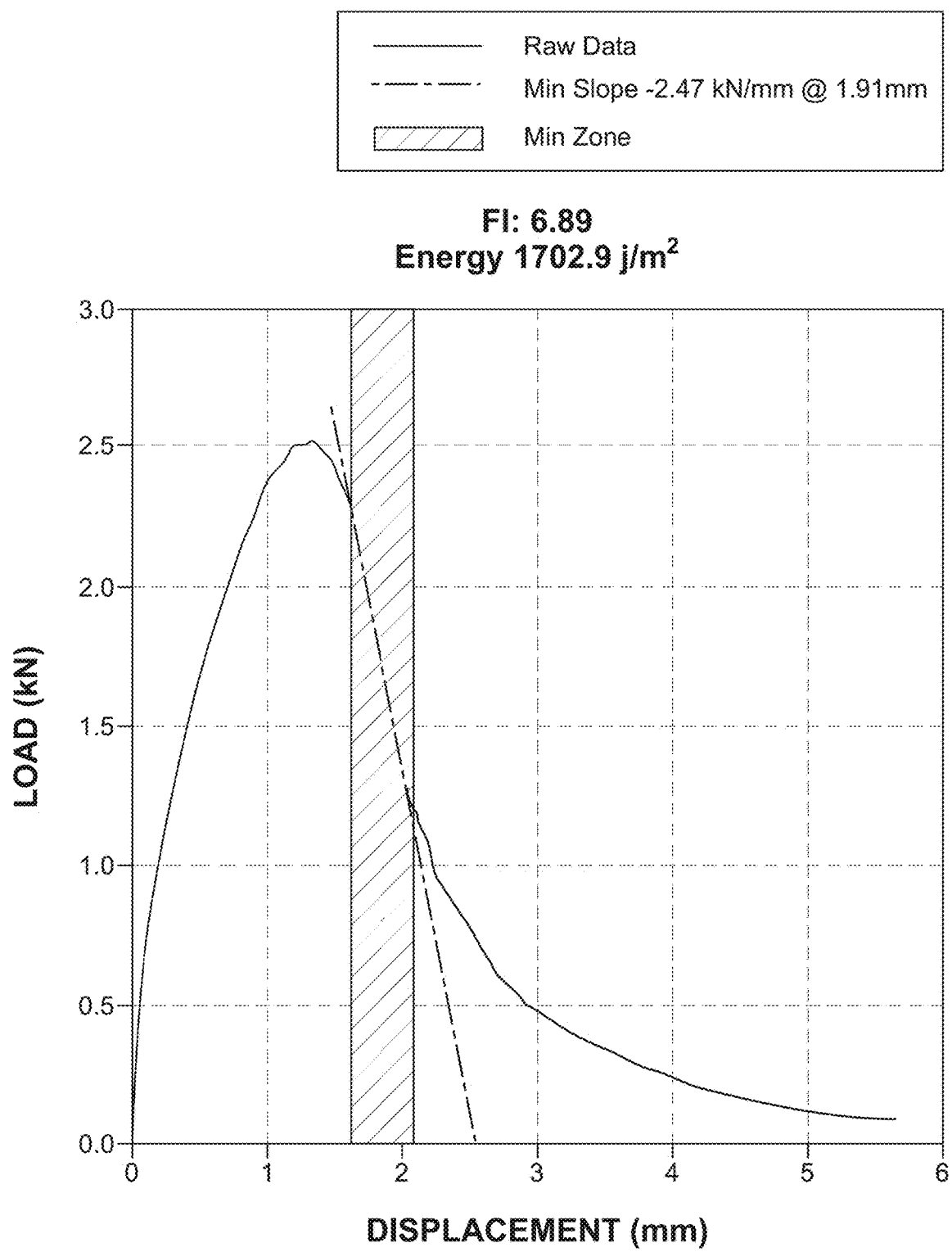
Figure 7B:
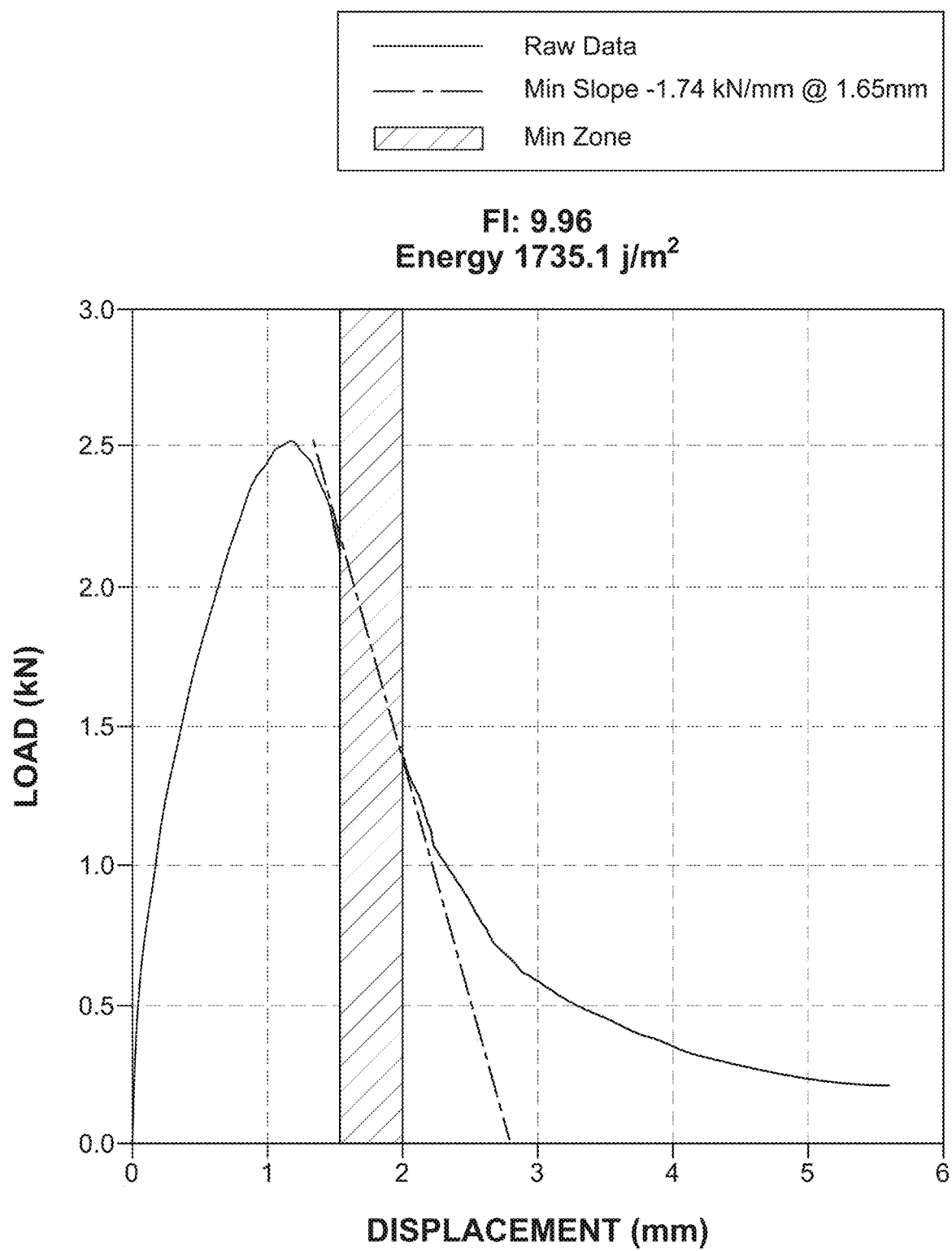
Figure 7C:
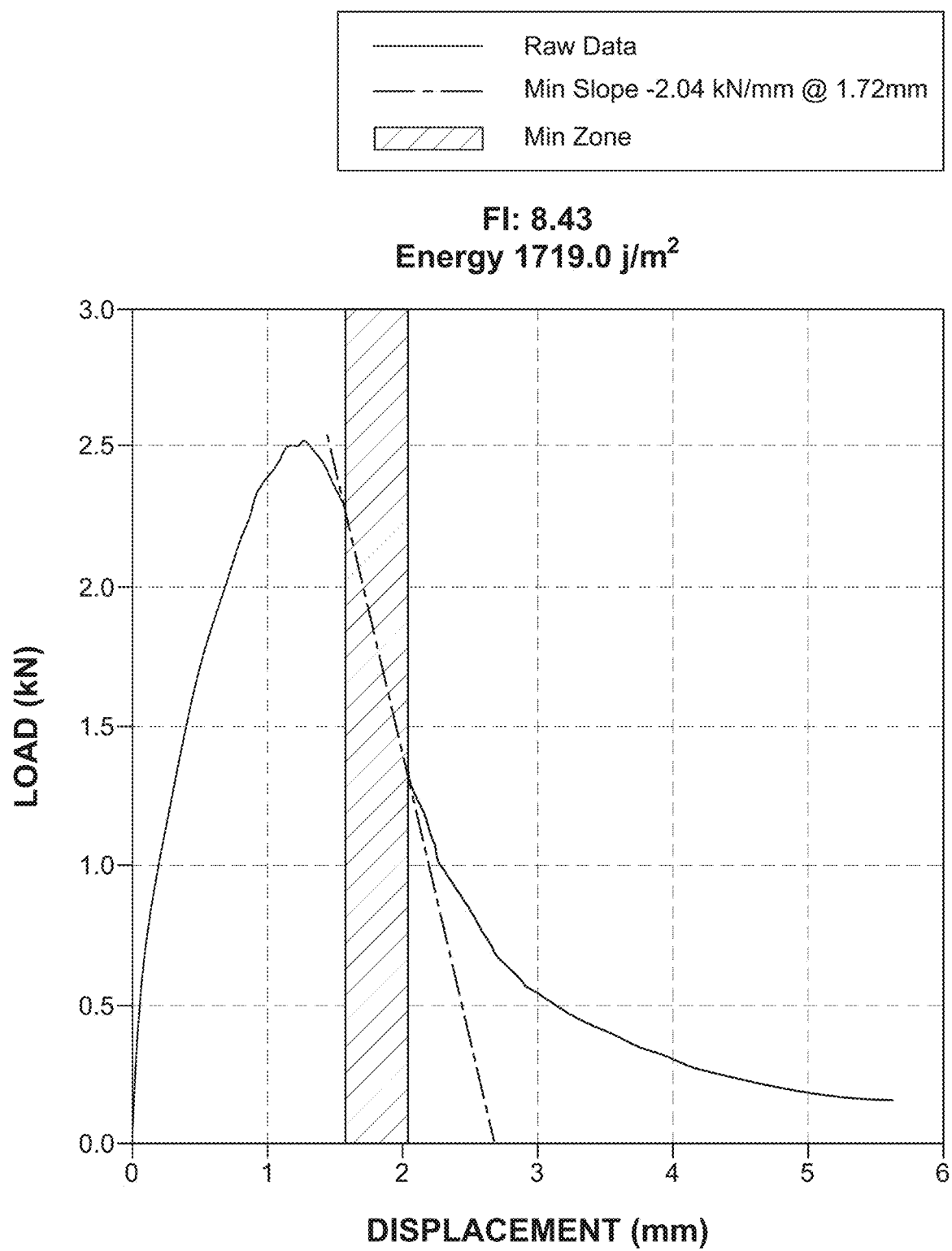

FIGS. 7A-C are graphs of example FI test results using the example control systems and apparatuses described above with regard to FIGS. 1-5. FIG. 7A depicts the results if only the left transducer (e.g., transducer 114a) were to be used to perform the test. FIG. 7B depicts the results if only the right transducer (e.g., transducer 114b) were to be used to perform the test. FIG. 7C depicts the results using a combination of both the left and right transducers (e.g., transducers 114a-b) to perform the test. Since shape of the plot is used in calculating test results, variably between left and right measurements leads to variable in calculated results. Using the previous example, a flexibility index (FI) is calculated for the left, right, and average values. Here each side (FIGS. 7A-B) has an 18% difference in flexibility index from the average (FIG. 7C).

Figure 8A:
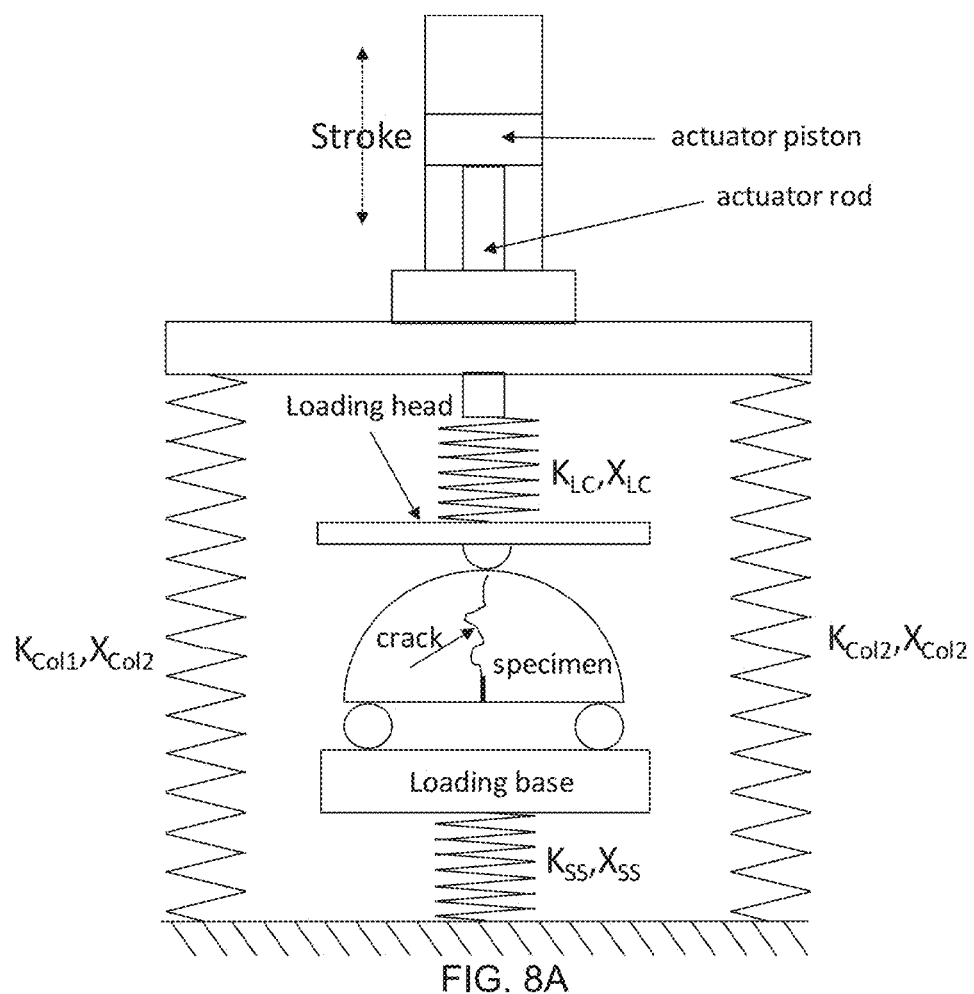
FIG. 8A depicts an example prior art device that measures displacement using stroke as the measure of LLD.

FIG. 8A depicts an example prior art device that measures displacement using stroke as the measure of LLD. One might ask, if measuring off a cantilevered point induces error, then why don't we measure off of the centerline of the actuator? The position of the actuator piston is often referred to as the "Stroke" measurement. Generally, the reference point of the actuator is a large distance away from the specimen. Since the deflection of any spring is a function of its length, the longer the distance from the specimen, the more deflection that is unaccounted for in the estimate of specimen deflection. Additionally, measuring the position the actuator does not take into account the deflection of the loading columns, load cell and support shaft. From example device depicted in FIG. 8A, as the piston compresses the specimen, the load columns will stretch, and the load cell and support column will compress. This leads to error in the specimen deformation measurement, as well as error in the control of the loading velocity.

Cost can be another issue with centerline actuator displacement measurements. Internal LVDTs, such as the one represented in FIG. 8A, inside a hydraulic actuator can be very expensive—much more expensive than the transducers and other position measuring devices described above with regard to FIGS. 1-7.

Figure 8B:
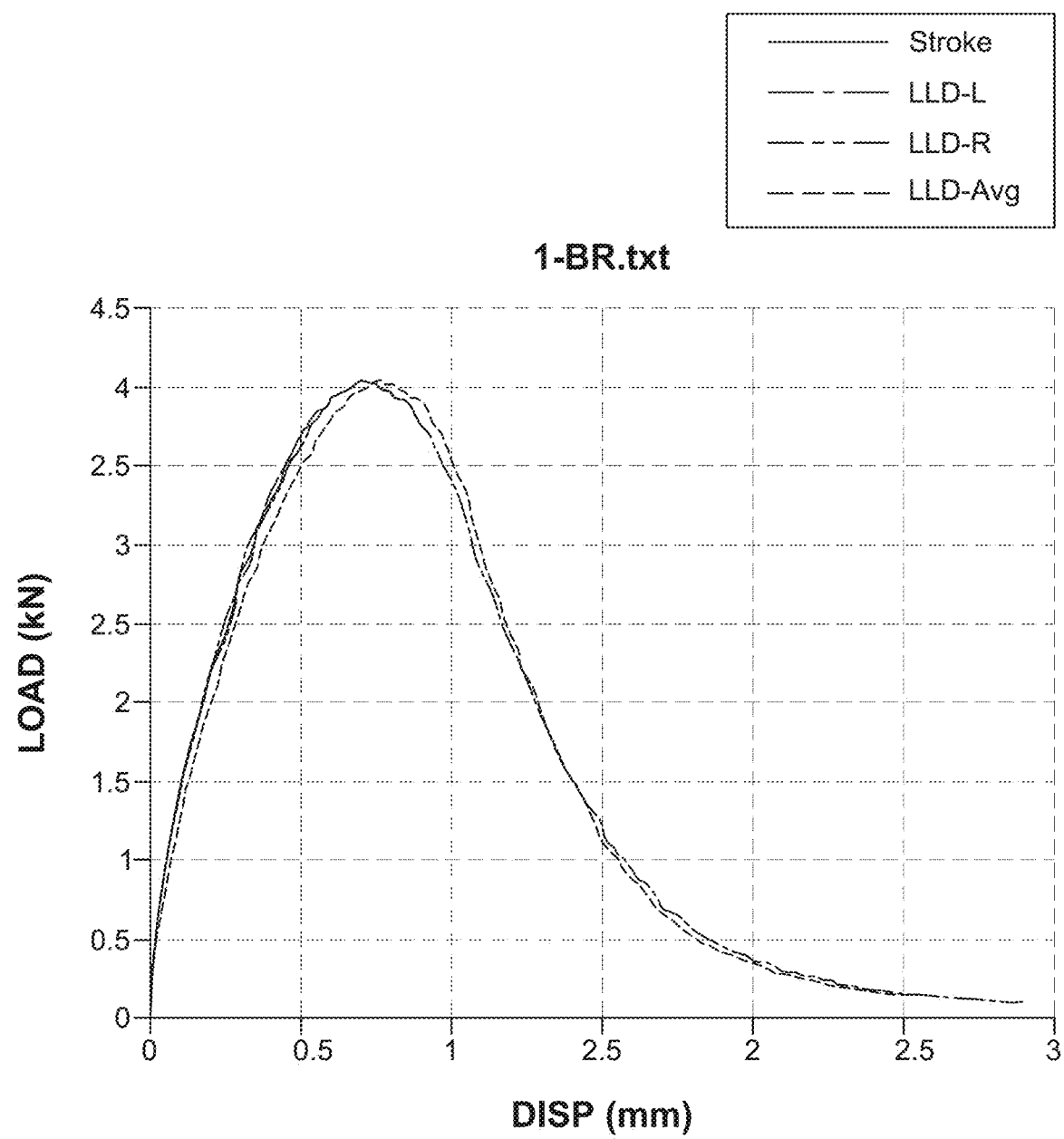
FIG. 8B is a graph comparing test results using stroke measurements to a combined displacement value determined from multiple transducers.

FIG. 8B is a graph comparing test results using stroke measurements, as described in FIG. 8A, to a combined displacement value determined from multiple transducers, as described in FIGS. 1-7 above. This example shows that, in some cases, there is very little variability between transducer 1 (LLD_L) and transducer 2 (LLD_R). In this case, transducer 1 was mounted on the "left" side of the machine and transducer 2 was mounted on the "right" side of the machine. This test also shows how there is typically more deflection measured at the actuator piston; measurement of the actuator piston is referred to as its "stroke." This is why the Load Line Displacement (LLD) measurement is more accurate for specimen testing than the Stroke measurement, even though stroke is along the centerline of the fixture.

Figures 9A, 9B, 9C:
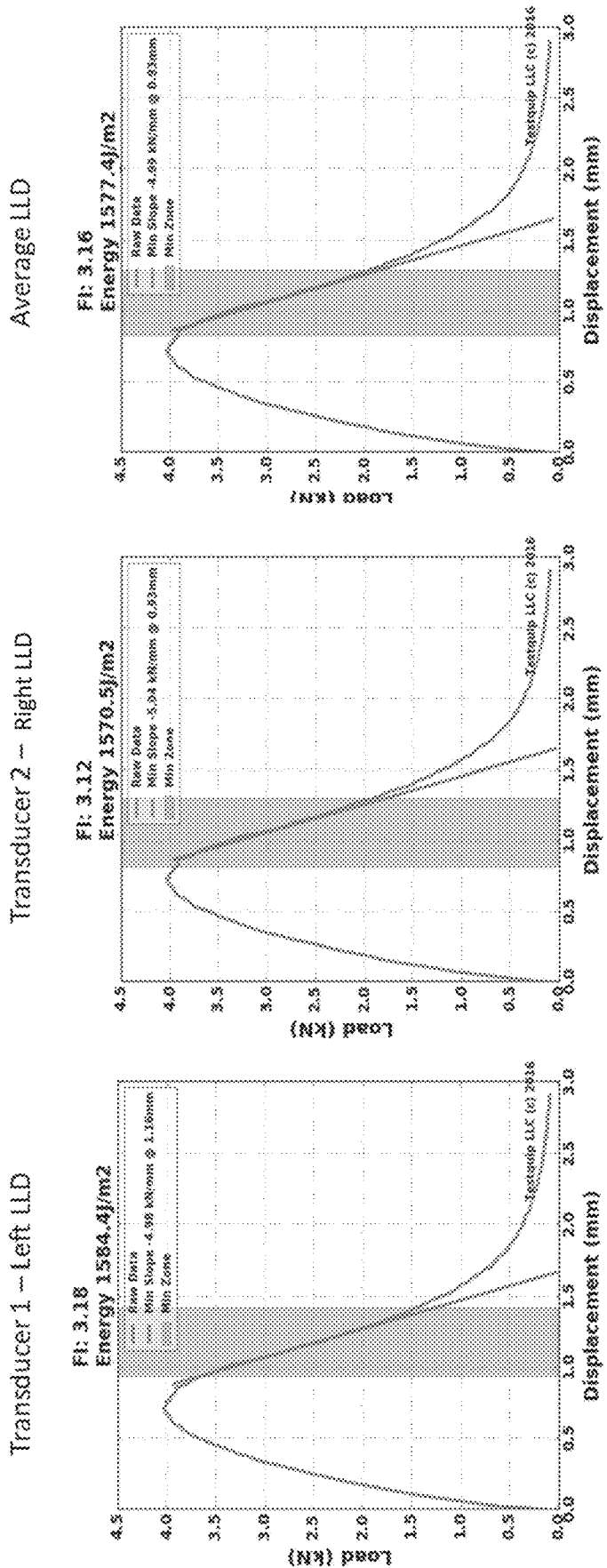

FIGS. 9A-E depict an example comparison of average LLD measurements versus a stroke displacement measurement. FIGS. 9A-C depict FI measurements for a left transducer (FIG. 9A), a right transducer (FIG. 9B), and an average of the two (FIG. 9C).

Using the previous example, in some cases there may not a significant difference between results calculated from a Left and Right transducer. In this case, the left and right flexibility index (FI) was within 1% of the average. Since the amount of bias is not always predictable, it is not reliable to assume that test results are unbiased; the only certain way to determine the bias is to measure it. The way to remove the bias is to cancel it out by combining the values, such as through averaging them.

FIGS. 9D-E provide a comparison of the average LLD determination (FIG. 9D) and measurements from an actuator stroke (FIG. 9E). The measurement of actuator stroke is not as reliable as Load Line Displacement (LLD). In the previous example, despite the fact that the results from the left and right LLD measurements were consistent with the average, the measurement of stroke was not consistent. The additional deflection picked up in the stroke measurement resulted in a 14% reduction in flexibility index (FI). Since a higher flexibility index value is desirable, measuring stroke falsely degrades the calculated results.

FIG. 10 is a photograph of another material testing apparatus that can use multiple displacement measuring devices for the load head to control testing in a feedback loop and to additionally provide improved testing results. In the depicted example, an indirect tension (IDT) testing machine is depicted, which is somewhat different from the SCB machines described above. In particular, with the IDT machine the specimen is a full disk instead of a half-disk like on the SCB machine. The frame consists of four posts for increased stiffness due to higher load capacity. The load cell is mounted to the base plate instead of the actuator rod. A single top and bottom loading strip of equal design are used to contact the specimen. The displacement transducers are mounted to the load cell, and the reference magnets are mounted to the sides of the loading head. Examples of an IDT machine are depicted above with regard to FIGS. 5A-C.

The features described above can be applied to other testing machines and control systems. For example, in addition to averaging values on two opposing sides of the loading fixture, a testing apparatus could include three, four, five, six, and/or other numbers of transducers providing values that are combined (e.g., averaged). If the bias in a loading frame and/or specimen is complex enough, additional transducers and reference locations may provide improved controllability and estimation of the deformation of the specimen under test. With three or more transducers, the bending movement can be resolved along more than one axis relative to the specimen. The techniques, systems, apparatuses, and devices described in this document can additionally be applied to performance tests that load the specimen in tension, and/or measure the deformation of the specimen through the use of displacement transducers and/or reference points mounted directly on the specimen. For example, the Disk-shaped Compact Tension (DCT) test (e.g., described by the ASTM D7313 standard) applies a tensile load to the specimen and uses a single clip-on displacement (COD) gauge mounted on the specimen to control and measure the rate of displacement at the specimen's crack mouth. The features described above can be applied to a DCT test in a variety of ways, such as through the inclusion and use of multiple displacement measuring devices (e.g., multiple displacement gauges). For example, a DCT test can be modified to include two displacement gauges that are mounted closer to the crack tip on both (left and right) sides of the specimen (see FIG. 11 for example side view of a DCT test specimen). Any non-uniform loading resulting from the interaction between the specimen and the tensile load fixtures, can lead to variability between the measurement on either side of the specimen. For improved controllability and measurement, the techniques described above can be applied to combine the measurements from these multiple displacement gauges to generate a more accurate combined measurement. Other variations and applications of the disclosed techniques, systems, apparatuses, and devices can be applied to DCT tests, other tensile load tests, and/or other compression tests. While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A material testing apparatus, the apparatus comprising:
an actuator to drive a load head according to electronic control signals, wherein the load head supplies a load to a material specimen in a first dimension, wherein the actuator applies the force to the load head;
a plurality of load line displacement (LLD) reference points that extend radially outward from the load head;
a plurality of LLD measuring devices that correspond to the plurality of LLD reference points, each of the plurality of LLD measuring devices (i) being positioned to detect a position of a corresponding LLD reference point along the first dimension and (ii) being configured to transmit position signals to a controller; and
a load cell to measure the load supplied to the material specimen by the load head, wherein the load cell is configured to transmit load signals to the controller,
wherein the controller is programmed to perform a performance test on the material specimen using (i) a combination of the position signals from the plurality of LLD measuring devices and (ii) the load signal from the load cell, and wherein the controller determines and provides the control signals to the actuator so that a target rate of LLD is achieved during the performance test, and
wherein the combination of position signals comprises an average of the position signals.

2. The apparatus of claim 1, wherein the plurality of LLD measuring devices comprise a plurality of transducers.

3. The apparatus of claim 2, wherein:
the plurality of LLD reference points comprise a plurality of magnets, and
the plurality of transducers comprise a plurality of non-contact magneto restrictive position transducers that measure the positions of the plurality of magnets along the first dimension.

4. The apparatus of claim 3, wherein the plurality of magnets extend at least partially radially outward from the load head in a second dimension that is perpendicular to the first dimension.

5. The apparatus of claim 3, wherein: the plurality of magnets extend from opposing sides of the load head, and the plurality of non-contact magneto restrictive position transducers are positioned on opposing sides of the material specimen.

6. The apparatus of claim 3, wherein the material specimen comprises an asphalt specimen.

7. The apparatus of claim 6, wherein:
the controller is programmed to perform a flexibility index (FI) test on the asphalt specimen using (i) feedback control based on a combination of the position signals from the plurality of non-contact magneto restrictive position transducers and (ii) the load signal from the load cell, and
the controller provides the control signals to the actuator according to the feedback control so that a target rate of LLD is achieved during the FI test.

8. The apparatus of claim 7, wherein the target rate of LLD is 50 mm/minute.

9. The apparatus of claim 7, wherein the combination of the position signals comprises an average of the position signals.

10. The apparatus of claim 1, wherein the controller is separate from the apparatus.

11. A material testing system, the system comprising:
an actuator to drive a load head according to electronic control signals;
a load head to supply a load to a material specimen in a first dimension, wherein the actuator applies the movement to the load head;
a plurality of load line displacement (LLD) reference points that extend radially outward from the load head;
a plurality of LLD measuring devices that correspond to the plurality of LLD reference points, each of the plurality of LLD measuring devices (i) being positioned to detect a position of a corresponding LLD reference point along the first dimension and (ii) being configured to transmit position signals;
a load cell to measure the load supplied to the material specimen by the load head, wherein the load cell is configured to transmit load signals; and
a controller configured to (i) perform feedback control of the actuator based, at least in part, on the position signals during a performance test of the material specimen, (ii) record data during the performance test including receiving the load signals from the load cell and the position data; and (iii) determine a result for the performance test based on the recorded data, wherein the feedback control comprises, repeatedly during the performance test:
receiving the position signals from the plurality of LLD measuring devices;
combining the position signals into a combined position;
determining an LLD measurement for the material specimen based on the combined position; and
comparing the LLD measurement with an target loading rate for the performance test, determine the control signals for the actuator based on the comparison, and provide the control signals to the actuator,
wherein combining the position signals comprises averaging the position signals and the combined position comprises an average position.

12. The system of claim 11, wherein: the performance test comprises an FI test, the material specimen comprises an asphalt specimen, the data that is recorded comprises the average position and the load signals, and the result for the FI test is an FI result value.

13. The system of claim 12, wherein the target loading rate comprises 50 mm/minute.

14. The system of claim 11, wherein:
the plurality of LLD measuring devices comprise a plurality of transducers,
the plurality of LLD reference points comprise a plurality of magnets,
the plurality of transducers comprise a plurality of non-contact magneto restrictive position transducers that measure the positions of the plurality of magnets along the first dimension,
the material specimen comprises an asphalt specimen,
the controller is programmed to perform a flexibility index (FI) test on the asphalt specimen using (i) feedback control based on a combination of the position signals from the plurality of non-contact magneto restrictive position transducers and (ii) the load signal from the load cell, and
the controller provides the control signals to the actuator according to the feedback control so that a target rate of LLD is achieved during the FI test.

15. The system of claim 14, wherein the target rate of LLD is 50 mm/minute.

16. A method for performing a performance test on a material specimen, the method comprising:
performing feedback control on a material testing apparatus that includes (i) an actuator moving a load head to supply a load to a material specimen, (ii) a plurality of load line displacement (LLD) reference points that extend radially outward from the load head, (iii) a plurality of LLD measuring devices to provide position signals indicating positions of the plurality of LLD reference points, and (iv) a load cell to provide load signals for the load supplied to the material specimen, the feedback control comprising repeatedly performing the following:
receiving the position signals from the plurality of LLD measuring devices, receiving the load signals from the load cell,
combining the position signals into a combined position,
determining an LLD measurement for the material specimen based on the combined position,
comparing the LLD measurement with a target loading rate for the performance test, determining the control signals for the actuator based on the comparison, and providing the control signals to the actuator; and
determining a result for the material specimen under the performance test based on, at least, the combined position and the load signals during the performance test,
wherein combining the position signals comprises averaging the position signals and the combined position comprises an average position.

* * * * *